US012573203B2

(12) United States Patent
Taki et al.

(10) Patent No.: US 12,573,203 B2
(45) Date of Patent: Mar. 10, 2026

(54) MEDICAL OBSERVATION SYSTEM, INFORMATION PROCESSING APPARATUS, AND INFORMATION PROCESSING METHOD

(71) Applicant: Sony Group Corporation, Tokyo (JP)

(72) Inventors: Yuhei Taki, Tokyo (JP); Yohei Kuroda, Tokyo (JP); Jun Arai, Tokyo (JP); Kohei Amano, Tokyo (JP); Takeo Inagaki, Tokyo (JP); Ryouhei Yasuda, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 219 days.

(21) Appl. No.: 18/681,549

(22) PCT Filed: Mar. 25, 2022

(86) PCT No.: PCT/JP2022/014740
§ 371 (c)(1),
(2) Date: Feb. 6, 2024

(87) PCT Pub. No.: WO2023/017651
PCT Pub. Date: Feb. 16, 2023

(65) Prior Publication Data
US 2024/0346826 A1     Oct. 17, 2024

(30) Foreign Application Priority Data
Aug. 13, 2021     (JP) .................................. 2021-131971

(51) Int. Cl.
*G06V 20/50*          (2022.01)
*A61B 1/00*           (2006.01)
(Continued)

(52) U.S. Cl.
CPC .......... *G06V 20/50* (2022.01); *A61B 1/00009* (2013.01); *A61B 1/0004* (2022.02);
(Continued)

(58) Field of Classification Search
None
See application file for complete search history.

(56) References Cited

U.S. PATENT DOCUMENTS 5,921,992 A * 7/1999 Costales ................ A61B 34/20
601/1
2015/0342460 A1* 12/2015 Izatt ..................... A61B 5/0073
600/425
(Continued)

FOREIGN PATENT DOCUMENTS

CN          112932663 A      6/2021
JP          H09-028663 A     2/1997
(Continued)

OTHER PUBLICATIONS

International Search Report and Written Opinion mailed on Jun. 7, 2022, received for PCT Application PCT/JP2022/014740, filed on Mar. 25, 2022, 8 pages including English Translation.

*Primary Examiner* — Talha M Nawaz
(74) *Attorney, Agent, or Firm* — XSENSUS LLP

(57) ABSTRACT
A medical observation system includes: an imaging unit that acquires an operative field image including an abdominal cavity environment; a display unit that displays the operative field image acquired by the imaging unit; a gaze information acquisition unit that acquires information regarding gaze of a user on the abdominal cavity environment of the operative field image displayed by the display unit; a target candidate recognition unit that recognizes a tracking target candidate from the operative field image acquired by the imaging unit; a reliability acquisition unit that acquires recognition reliability of the tracking target candidate recognized by the
(Continued)

IMAGE RECOGNITION STATE

LINE-OF-SIGHT STATE/ RETENTION STATE

IMAGE RECOGNITION+ LINE-OF-SIGHT STATE

TRACKING STATE target candidate recognition unit; and a target determination unit that determines a tracking target in the abdominal cavity environment from the tracking target candidate on the basis of the information regarding the tracking target candidate, the recognition reliability, and the information regarding the gaze.

23 Claims, 17 Drawing Sheets

(51) Int. Cl.

| | |
|---|---|
| *A61B 1/313* | (2006.01) |
| *G06F 3/01* | (2006.01) |
| *G06V 10/22* | (2022.01) |
| *H04N 23/695* | (2023.01) |

(52) U.S. Cl.

CPC ........ *A61B 1/00045* (2013.01); *A61B 1/3132* (2013.01); *G06F 3/013* (2013.01); *G06V 10/235* (2022.01); *H04N 23/695* (2023.01); *G06V 2201/034* (2022.01)

(56) References Cited

U.S. PATENT DOCUMENTS

| | | | |
|---|---|---|---|
| 2016/0000515 A1* | 1/2016 | Sela ........................ | A61B 34/10 |
| | | | 600/424 |
| 2017/0027650 A1* | 2/2017 | Merck ................ | A61B 1/00011 |

FOREIGN PATENT DOCUMENTS

| | | | |
|---|---|---|---|
| JP | 2012-518504 A | 8/2012 |
| WO | 2017/183353 A1 | 10/2017 |
| WO | 2018/159155 A1 | 9/2018 |
| WO | 2019/087904 A1 | 5/2019 |

* cited by examiner

FIG.5

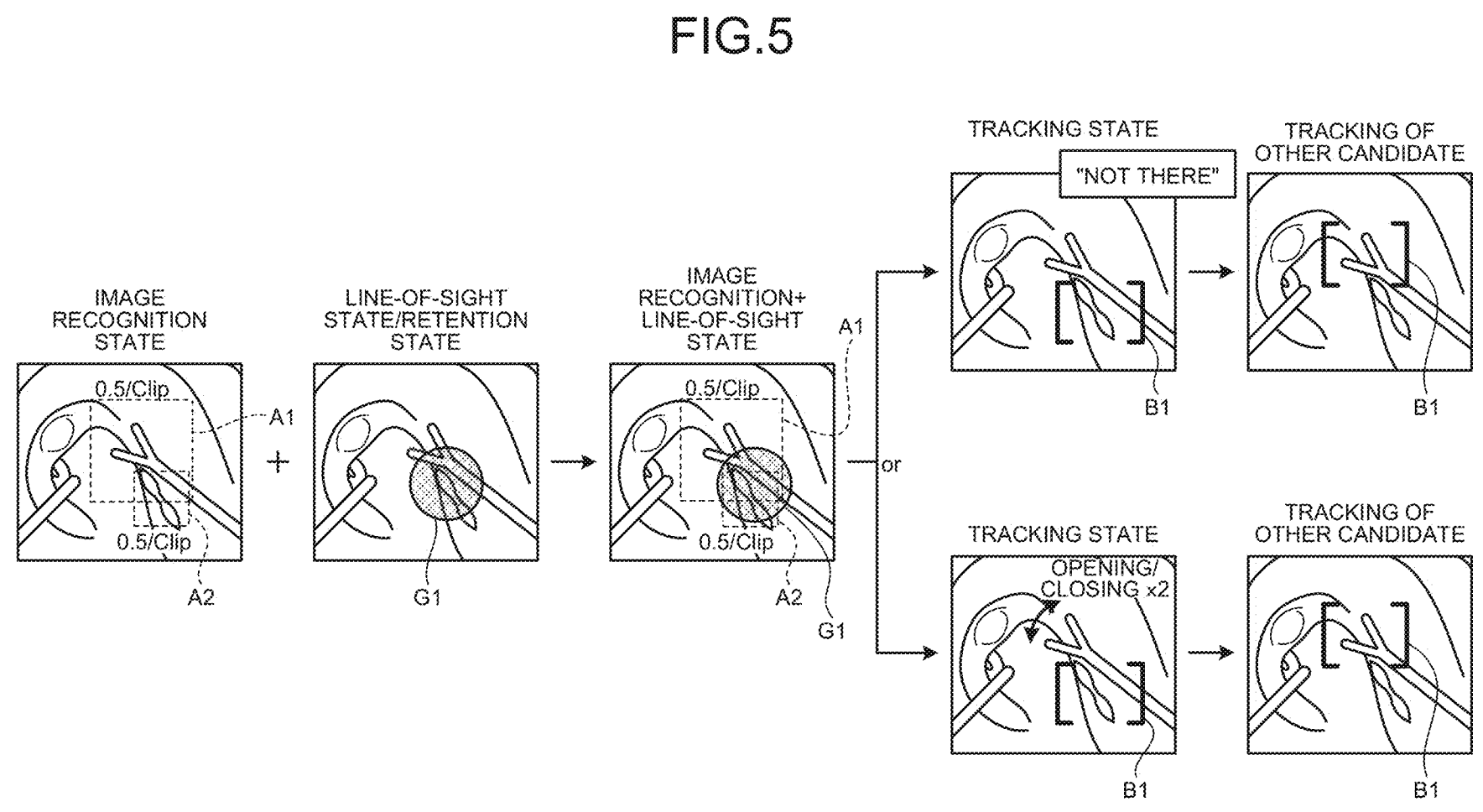

IMAGE RECOGNITION STATE

A1

A2

0.5/Clip 0.5/Clip

+

LINE-OF-SIGHT STATE/RETENTION STATE

G1

IMAGE RECOGNITION+ LINE-OF-SIGHT STATE

A1

A2

G1

0.5/Clip 0.5/Clip or

TRACKING STATE

"NOT THERE"

B1

TRACKING OF OTHER CANDIDATE

B1

TRACKING STATE

OPENING/ CLOSING ×2

B1

TRACKING OF OTHER CANDIDATE

MEDICAL OBSERVATION SYSTEM, INFORMATION PROCESSING APPARATUS, AND INFORMATION PROCESSING METHOD

CROSS-REFERENCE TO RELATED APPLICATIONS

The present application is based on PCT filing PCT/JP2022/014740, filed Mar. 25, 2022, which claims priority from Japanese Patent Application No. 2021-131971, filed Aug. 13, 2021, the entire contents of each are incorporated herein by reference.

FIELD

The present disclosure relates to a medical observation system, an information processing apparatus, and an information processing method.

BACKGROUND

Normally, in endoscopic surgery, the abdominal cavity of a patient is imaged by an endoscope, and the captured operative field image in the abdominal cavity is displayed by a display. The operator performs surgery while confirming the operative field image displayed on the display. In such an endoscopic surgery system, a system that recognizes a surgical instrument in the abdominal cavity by image recognition processing and performs imaging tracking the surgical instrument has been developed. In addition, a system for obtaining an appropriate operative field image by a method other than image recognition has also been proposed (see, for example, Patent Literatures 1 and 2).

CITATION LIST

Patent Literature

Patent Literature 1: JP 2012-518504 A
Patent Literature 2: JP H9-28663 A

SUMMARY

Technical Problem

However, in the above-described image recognition based surgical instrument automatic tracking (for example, a target, a position, a speed, and the like), in a situation where the image recognition cannot be performed well, an operation (for example, different instrument types, positions, zoom ratios, or the like) different from expectation may occur, and the automatic tracking accuracy with respect to the tracking target is insufficient. In addition, since the search for the endoscopic surgery system that autonomously performs the tracking operation has not yet progressed, and the development regarding the cooperation between the autonomous system and the user intention has not been sufficiently performed, the automatic tracking accuracy with respect to the tracking target is insufficient.

Therefore, the present disclosure proposes a medical observation system, an information processing apparatus, and an information processing method capable of improving automatic tracking accuracy for a tracking target.

Solution to Problem

A medical observation system according to the embodiment of the present disclosure includes: an imaging unit that acquires an operative field image including an abdominal cavity environment; a display unit that displays the operative field image acquired by the imaging unit; a gaze information acquisition unit that acquires information regarding gaze of a user on the abdominal cavity environment of the operative field image displayed by the display unit; a target candidate recognition unit that recognizes a tracking target candidate from the operative field image acquired by the imaging unit; a reliability acquisition unit that acquires recognition reliability of the tracking target candidate recognized by the target candidate recognition unit; and a target determination unit that determines a tracking target in the abdominal cavity environment from the tracking target candidate on a basis of the information regarding the tracking target candidate recognized by the target candidate recognition unit, the recognition reliability acquired by the reliability acquisition unit, and the information regarding the gaze acquired by the gaze information acquisition unit.

An information processing apparatus according to the embodiment of the present disclosure includes: a target candidate recognition unit that recognizes a tracking target candidate from an operative field image acquired by an imaging unit that acquires the operative field image including an abdominal cavity environment; a reliability acquisition unit that acquires recognition reliability of the tracking target candidate recognized by the target candidate recognition unit; a gaze information acquisition unit that acquires information regarding gaze of a user on the abdominal cavity environment of the operative field image displayed by a display unit that displays the operative field image acquired by the imaging unit; and a tracking target determination unit that determines a tracking target in the abdominal cavity environment from the tracking target candidate on a basis of the information regarding the tracking target candidate recognized by the target candidate recognition unit, the recognition reliability acquired by the reliability acquisition unit, and the information regarding the gaze acquired by the gaze information acquisition unit.

An information processing method according to the embodiment of the present disclosure includes: recognizing a tracking target candidate from an operative field image acquired by an imaging unit that acquires the operative field image including an abdominal cavity environment; acquiring recognition reliability of the tracking target candidate recognized; acquiring information regarding gaze of a user on the abdominal cavity environment of the operative field image displayed by a display unit that displays the operative field image acquired by the imaging unit; and determining a tracking target in the abdominal cavity environment from the tracking target candidate on a basis of the information regarding the tracking target candidate recognized, the recognition reliability acquired, and the information regarding the gaze acquired.

BRIEF DESCRIPTION OF DRAWINGS

FIG. 5 is a diagram for explaining a third processing example according to an embodiment of the present disclosure.

FIG. 6 is a diagram for explaining a fourth processing example according to an embodiment of the present disclosure.

FIG. 8 is a diagram for explaining a sixth processing example according to an embodiment of the present disclosure.

DESCRIPTION OF EMBODIMENTS

Hereinafter, embodiments of the present disclosure will be described in detail with reference to the drawings. Note that the system, the device, the method, and the like according to the present disclosure are not limited by the embodiments. In addition, in the present specification and the drawings, components having substantially the same functional configurations are basically denoted by the same reference signs, and redundant description is omitted.

One or more embodiments (including examples and modifications) described below can each be implemented independently. Meanwhile, at least some of the plurality of embodiments described below may be appropriately combined with at least some of other embodiments. The plurality of embodiments may include novel features different from each other. Therefore, the plurality of embodiments can contribute to solving different objects or problems, and can exhibit different effects.

The present disclosure will be described according to the following order of items.

1. Embodiments
1-1. Configuration Example of Endoscopic Surgery System
1-1-1. Schematic Configuration Example of Endoscopic Surgery System
1-1-2. Detailed Configuration Example of Support Arm Device
1-1-3. Detailed Configuration Example of Light Source Device
1-1-4. Detailed Configuration Example of Camera Head, Input Device, and CCU
1-2. Processing Example Related to Tracking Target Determination
1-2-1. First Processing Example
1-2-2. Second Processing Example
1-2-3. Third Processing Example
1-2-4. Fourth Processing Example
1-2-5. Fifth Processing Example
1-2-6. Sixth Processing Example
1-2-7. Seventh Processing Example
1-2-8. GUI Variations
1-3. Example of Tracking Processing of Endoscopic Surgery System
1-3-1. Overall Process Flow
1-3-2. Flow During Main Steps in Entire Process
1-4. Example of Trigger Operation for Start and Stop of Automatic Tracking and Voice Input
1-5. Actions and Effects
2. Other Embodiments
3. Application Example
4. Configuration Example of Hardware
5. Appendix

1. EMBODIMENTS

1-1. Configuration Example of Endoscopic Surgery System

1-1-1. Schematic Configuration Example of Endoscopic Surgery System

Figure 1:
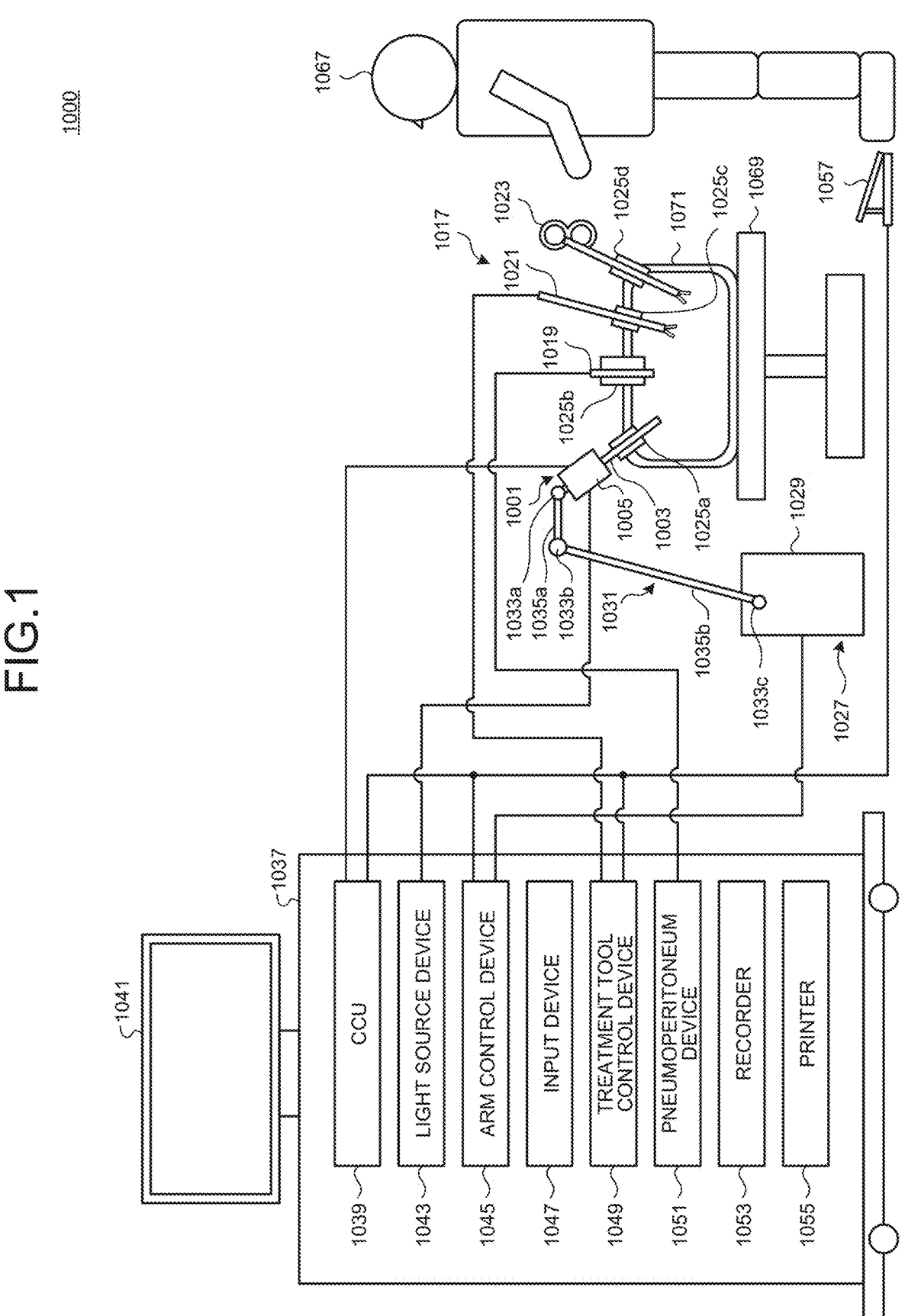
FIG. 1 is a diagram illustrating an example of a schematic configuration of an endoscopic surgery system according to an embodiment of the present disclosure.

An example of a schematic configuration of an endoscopic surgery system 1000 according to the present embodiment will be described with reference to FIG. 1. FIG. 1 is a diagram illustrating an example of a schematic configuration of the endoscopic surgery system 1000 according to the present embodiment. The endoscopic surgery system 1000 includes a medical observation system.

FIG. 1 illustrates a state in which an operator 1067 such as a doctor is performing surgery on a patient 1071 on a patient bed 1069 using the endoscopic surgery system 1000. As illustrated in FIG. 1, the endoscopic surgery system 1000 includes an endoscope 1001, other surgical tools 1017, a support arm device 1027 that supports the endoscope 1001, and a cart 1037 on which various devices for endoscopic surgery are mounted.

In endoscopic surgery, instead of cutting the abdominal wall and opening the abdomen, for example, a plurality of cylindrical puncture instruments called trocars 1025a to 1025d is punctured into the abdominal wall. Then, a lens barrel 1003 of the endoscope 1001 and the other surgical tools 1017 are inserted into the body cavity of the patient 1071 from the trocars 1025a to 1025d. In the example of FIG. 1, as the other surgical tools 1017, a pneumoperitoneum tube 1019, an energy treatment tool 1021, and forceps 1023 are inserted into the body cavity of the patient 1071. Furthermore, the energy treatment tool 1021 is a treatment tool that performs incision and detachment of tissue, sealing of a blood vessel, or the like by high-frequency current or ultrasonic vibration. However, the surgical tools 1017 illustrated in FIG. 1 are merely examples, and various instruments generally used in endoscopic surgery, such as tweezers and a retractor, for example, may be used as the surgical tools 1017.

An image of the surgical site in the body cavity of the patient 1071 captured by the endoscope 1001 is displayed on a display device 1041. While viewing the image of the surgical site displayed on the display device 1041 in real time, the operator 1067 performs treatment such as resection of an affected part using the energy treatment tool 1021 and the forceps 1023. Note that, although not illustrated, the pneumoperitoneum tube 1019, the energy treatment tool 1021, and the forceps 1023 are supported by, for example, the operator 1067, an assistant, or the like during surgery.

(Support Arm Device)

The support arm device 1027 includes an arm portion 1031 extending from a base portion 1029. In the example of FIG. 1, the arm portion 1031 includes a plurality of joint portions 1033a, 1033b, and 1033c and a plurality of links 1035a and 1035b, and is driven under the control of an arm control device 1045. The endoscope 1001 is supported by the arm portion 1031, and its position and posture are controlled. As a result, stable fixation of the position of the endoscope 1001 can be implemented. The rotational drive of each of the joint portions 1033a, 1033b, and 1033c is controlled by control from the arm control device 1045 to drive the arm portion 1031. Note that the arm portion 1031 may include a motion sensor (not illustrated) including an acceleration sensor, a gyro sensor, a geomagnetic sensor, and the like in order to obtain information on the position and posture of the arm portion 1031.

(Endoscope)

The endoscope 1001 includes the lens barrel 1003 whose region of a predetermined length from the distal end is inserted into the body cavity of the patient 1071, and a camera head 1005 connected to the proximal end of the lens barrel 1003. In the example of FIG. 1, the endoscope 1001 configured as a so-called rigid scope having a rigid lens barrel 1003 is illustrated, but the endoscope 1001 may be configured as a so-called flexible scope having a flexible lens barrel 1003, and is not particularly limited.

An opening portion into which an objective lens is fitted is provided at the distal end of the lens barrel 1003. A light source device 1043 is connected to the endoscope 1001, and light generated by the light source device 1043 is guided to the distal end of the lens barrel 1003 by a light guide extending inside the lens barrel 1003, and is emitted toward an observation target in the body cavity of the patient 1071 via the objective lens. Note that the endoscope 1001 may be a forward-viewing endoscope, an oblique-viewing endoscope, or a side-viewing endoscope, and is not particularly limited.

An optical system and an imaging element (for example, the image sensor) are provided inside the camera head 1005, and reflected light (observation light) from the observation target is condensed on the imaging element by the optical system. The observation light is photoelectrically converted by the imaging element, and an electric signal corresponding to the observation light, that is, an image signal corresponding to the observation image is generated. The image signal is transmitted to a camera control unit (CCU) 1039 as RAW data. Note that the camera head 1005 is equipped with a function of adjusting the magnification and the focal length by appropriately driving the optical system.

Note that, for example, in order to support stereoscopic viewing (3D display) or the like, a plurality of imaging elements may be provided in the camera head 1005. In this case, a plurality of relay optical systems is provided inside the lens barrel 1003 in order to guide the observation light to each imaging element.

(Various Devices Mounted on Cart)

The CCU 1039 includes a central processing unit (CPU), a graphics processing unit (GPU), and the like, and integrally controls operation of the endoscope 1001 and the display device 1041. Specifically, the CCU 1039 performs, on the image signal received from the camera head 1005, various types of image processing for displaying an image based on the image signal, such as development processing (demosaic processing), for example. The CCU 1039 provides the image signal subjected to the image processing to the display device 1041. Furthermore, the CCU 1039 transmits a control signal to the camera head 1005 and controls driving thereof. The control signal can include information regarding imaging conditions such as magnification and focal length.

The display device 1041 displays an image based on the image signal subjected to the image processing by the CCU 1039 under the control of the CCU 1039. In a case where the endoscope 1001 is compatible with high-resolution imaging such as 4K (the number of horizontal pixels 3840×the number of vertical pixels 2160) or 8K (the number of horizontal pixels 7680×the number of vertical pixels 4320), and/or in a case where the endoscope is compatible with 3D display, for example, a display device capable of high-resolution display and/or a display device capable of 3D display can be used as the display device 1041 corresponding to each case. In a case where the display device is compatible with high resolution imaging such as 4K or 8K, a further immersive feeling can be obtained by using a display device having a size of 55 inches or more as the display device 1041. The display device 1041 is implemented by, for example, a liquid crystal display, an organic electro-luminescence (EL) display, or the like. Note that a plurality of display devices 1041 having different resolutions and sizes may be provided depending on the application. The display device 1041 corresponds to a display unit.

The light source device 1043 includes a light source such as a light emitting diode (LED), for example, and supplies irradiation light to the endoscope 1001 when imaging a surgical site to be imaged. For example, the light source device 1043 may be configured by combining an LED and a lens to diffuse light. Furthermore, the light source device 1043 may have a configuration in which light transmitted through an optical fiber (light guide) is diffused by a lens. In addition, the light source device 1043 may expand the irradiation range by irradiating the optical fiber itself with light in a plurality of directions.

The arm control device 1045 includes, for example, a processor such as a CPU, and operates according to a predetermined program to control driving of the arm portion 1031 of the support arm device 1027 according to a predetermined control method. Specifically, the arm control device 1045 integrally controls the support arm device 1027 and controls driving of the arm portion 1031. That is, the arm control device 1045 controls the driving of the arm portion 1031 by controlling the driving of the joint portions 1033a, 1033b, and 1033c. Specifically, the arm control device 1045 controls the number of rotations of the motor by controlling the amount of current supplied to the motor in each actuator of each of the joint portions 1033*a*, 1033*b*, and 1033*c*, and controls the rotation angle and the generated torque in each of the joint portions 1033*a*, 1033*b*, and 1033*c*. For example, the arm control device 1045 can autonomously control the position and posture of the arm portion 1031 according to input information received by an input device 1047, information based on an image signal received from the camera head 1005, and the like. The arm control device 1045 corresponds to an arm control unit.

The input device 1047 is an input interface for the endoscopic surgery system 1000. The user can input various types of information and instructions to the endoscopic surgery system 1000 via the input device 1047. For example, the user inputs various types of information regarding surgery, such as physical information of a patient and information regarding a surgical procedure of the surgery, via the input device 1047. Furthermore, for example, the user inputs an instruction to drive the arm portion 1031, an instruction to change imaging conditions (type, magnification, focal length, and the like of irradiation light) by the endoscope 1001, an instruction to drive the energy treatment tool 1021, and the like via the input device 1047.

Note that the type of the input device 1047 is not particularly limited, and the input device 1047 may be various known input devices. As the input device 1047, for example, a mouse, a keyboard, a touch panel, a switch, a foot switch 1057, a lever, and/or the like can be applied. In a case where a touch panel is used as the input device 1047, the touch panel may be provided on the display surface of the display device 1041. Alternatively, the input device 1047 is, for example, a device worn by the user such as the operator 1067, such as a glasses-type wearable device or a head mounted display (HMD), and various inputs are performed according to a gesture or a line of sight of the user detected by these devices. Furthermore, the input device 1047 includes a camera capable of detecting movement of the user, and various inputs are performed according to a gesture or a line of sight of the user detected from a video captured by the camera. Furthermore, the input device 1047 includes a microphone capable of collecting user's voice, and various inputs are performed by voice via the microphone. As described above, since the input device 1047 is configured to be able to input various types of information in a non-contact manner, in particular, a user such as the operator 1067 belonging to a clean area can operate a device belonging to an unclean area in a non-contact manner. Furthermore, since the user can operate the device without releasing the hand from the surgical tool 1017 possessed by the user, the convenience of the user is improved.

A treatment tool control device 1049 controls driving of the energy treatment tool 1021 for cauterization and incision of tissue, sealing of a blood vessel, or the like. A pneumoperitoneum device 1051 feeds gas into the body cavity of the patient 1071 via the pneumoperitoneum tube 1019 in order to inflate the body cavity for the purpose of securing a visual field by the endoscope 1001 and securing a working space of the operator 1067. A recorder 1053 is a device capable of recording various types of information regarding surgery. A printer 1055 is a device capable of printing various types of information regarding surgery in various formats such as text, image, or graph.

1-1-2. Detailed Configuration Example of Support Arm Device

An example of a detailed configuration of the support arm device 1027 according to the present embodiment will be described with reference to FIG. 1.

As illustrated in FIG. 1, the support arm device 1027 includes the base portion 1029 which is a base, and the arm portion 1031 extending from the base portion 1029. In the example of FIG. 1, the arm portion 1031 includes the plurality of joint portions 1033*a*, 1033*b*, and 1033*c* and the plurality of links 1035*a* and 1035*b* connected by the joint portion 1033*b*, but in FIG. 1, the configuration of the arm portion 1031 is illustrated in a simplified manner for the sake of simplicity. Actually, the shapes, the number, and the arrangement of the joint portions 1033*a* to 1033*c* and the links 1035*a* and 1035*b*, the directions of the rotation axes of the joint portions 1033*a* to 1033*c*, and the like can be appropriately set so that the arm portion 1031 has a desired degree of freedom. For example, the arm portion 1031 can be suitably configured to have six degrees of freedom or more. As a result, since the endoscope 1001 can be freely moved within the movable range of the arm portion 1031, the lens barrel 1003 of the endoscope 1001 can be inserted into the body cavity of the patient 1071 from a desired direction.

Actuators are provided in the joint portions 1033*a* to 1033*c*, and the joint portions 1033*a* to 1033*c* are configured to be rotatable around a predetermined rotation axis by driving of the actuators. The driving of the actuator is controlled by the arm control device 1045, whereby the rotation angle of each of the joint portions 1033*a* to 1033*c* is controlled, and the driving of the arm portion 1031 is controlled. As a result, control of the position and posture of the endoscope 1001 can be implemented. At this time, the arm control device 1045 can control the driving of the arm portion 1031 by various known control methods such as force control or position control.

For example, by the operator 1067 appropriately performing an operation input via the input device 1047 (including the foot switch 1057), the driving of the arm portion 1031 may be appropriately controlled by the arm control device 1045 according to the operation input, and the position and posture of the endoscope 1001 may be controlled. With this control, the endoscope 1001 at the distal end of the arm portion 1031 can be moved from an arbitrary position to an arbitrary position and then fixedly supported at the position after the movement. Note that the arm portion 1031 may be operated by a so-called master-slave method. In this case, the arm portion 1031 (slave) can be remotely operated by the user via the input device 1047 (master console) installed at a place away from the operating room or in the operating room.

Furthermore, in a case where the force control is applied, the arm control device 1045 may perform so-called power assist control of receiving an external force from the user and driving the actuators of the joint portions 1033*a*, 1033*b*, and 1033*c* such that the arm portion 1031 smoothly moves according to the external force. As a result, when the user moves the arm portion 1031 while directly touching the arm portion 1031, the arm portion 1031 can be moved with a relatively light force. Therefore, it is possible to more intuitively move the endoscope 1001 with a simpler operation, and the convenience of the user can be improved.

Here, in general, in endoscopic surgery, the endoscope 1001 is supported by a doctor called scopist. On the other hand, by using the support arm device 1027, it is possible to more reliably fix the position of the endoscope 1001 without manual operation, so that it is possible to stably obtain an image of the surgical site and smoothly perform the surgery.

Note that, although the arm portion 1031 of the support arm device 1027 has been described as having the plurality of joint portions 1033*a*, 1033*b*, and 1033*c* and having a plurality of degrees of freedom, the invention is not limited thereto. Specifically, the arm portion 1031 is only required to have a structure in which the endoscope 1001 or an exoscope is provided at the distal end. For example, the arm portion 1031 may have a configuration having only one degree of freedom for driving the endoscope 1001 to move in a direction of entering the body cavity of the patient and a direction of retracting.

Furthermore, the arm control device 1045 is not necessarily provided in the cart 1037. Furthermore, the arm control device 1045 is not necessarily one device. For example, the arm control device 1045 may be provided in each of the joint portions 1033a to 1033c of the arm portion 1031 of the support arm device 1027, and the drive control of the arm portion 1031 may be implemented by the plurality of arm control devices 1045 cooperating with each other.

1-1-3. Detailed Configuration Example of Light Source Device

An example of a detailed configuration of the light source device 1043 according to the present embodiment will be described with reference to FIG. 1.

As illustrated in FIG. 1, the light source device 1043 supplies irradiation light for imaging a surgical site to the endoscope 1001. The light source device 1043 includes, for example, an LED, a laser light source, or a white light source including a combination thereof. At this time, in a case where the white light source is configured by a combination of RGB laser light sources, the output intensity and the output timing of each color (each wavelength) can be controlled with high accuracy, so that the white balance of the captured image can be adjusted in the light source device 1043. Furthermore, in this case, by irradiating the observation target with the laser light from each of the RGB laser light sources in a time division manner and controlling the driving of the imaging element of the camera head 1005 in synchronization with the irradiation timing, it is also possible to capture an image corresponding to each of RGB in a time division manner. According to this method, a color image can be obtained without providing a color filter in the imaging element.

Furthermore, the driving of the light source device 1043 may be controlled so as to change the intensity of light to be output every predetermined time. By controlling the driving of the imaging element of the camera head 1005 in synchronization with the timing of the change of the light intensity to acquire images in a time division manner and synthesizing the images, it is possible to generate an image of a high dynamic range without so-called underexposed blocked up shadow and overexposed highlight.

Furthermore, the light source device 1043 may be configured to be able to supply light in a predetermined wavelength band corresponding to special light observation. In the special light observation, for example, so-called narrow band imaging is performed in which a predetermined tissue such as a blood vessel in a superficial portion of the mucous membrane is imaged with high contrast by irradiating light in a narrower band than irradiation light (that is, white light) at the time of normal observation using wavelength dependency of light absorption in a body tissue. Alternatively, in the special light observation, fluorescence observation for obtaining an image by fluorescence generated by irradiation with excitation light may be performed. In the fluorescence observation, for example, fluorescence from a body tissue can be observed by irradiating the body tissue with excitation light (autofluorescence observation), or a fluorescent image can be obtained by locally injecting a reagent such as indocyanine green (ICG) into a body tissue and irradiating the body tissue with excitation light corresponding to a fluorescence wavelength of the reagent. The light source device 1043 can be configured to be able to supply narrow band light and/or excitation light corresponding to such special light observation.

1-1-4. Detailed Configuration Example of Camera Head, Input Device, and CCU

Figure 2:
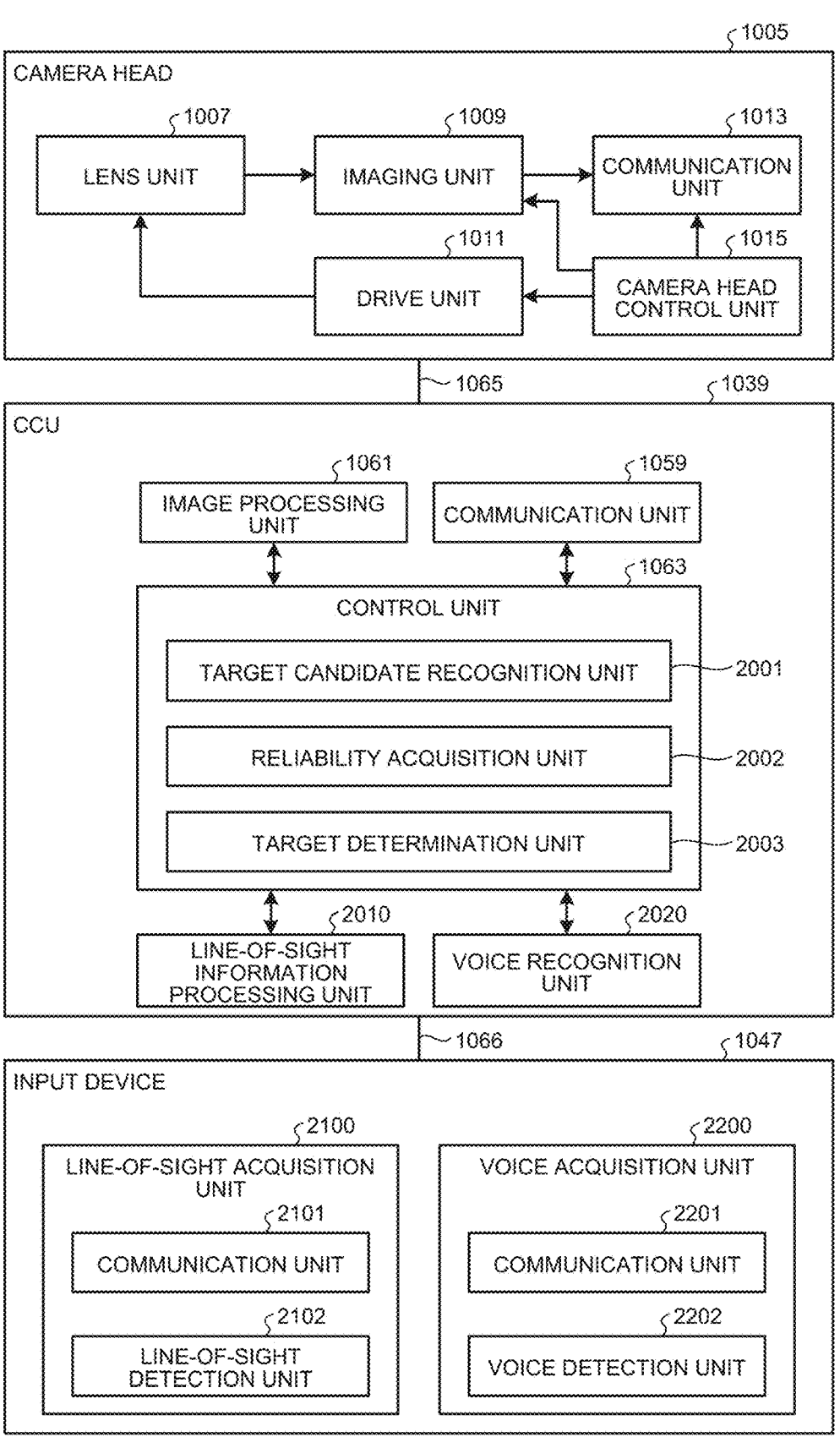
FIG. 2 is a diagram illustrating an example of a detailed configuration of a camera head, an input device, and a camera control unit (CCU) according to an embodiment of the present disclosure.

An example of a detailed configuration of the camera head 1005, the input device 1047, and the CCU 1039 of the endoscope 1001 according to the present embodiment will be described with reference to FIG. 2. FIG. 2 is a diagram illustrating an example of a detailed configuration of the camera head 1005, the input device 1047, and the CCU 1039 according to the present embodiment.

As illustrated in FIG. 2, the camera head 1005 includes, as functions thereof, a lens unit 1007, an imaging unit 1009, a drive unit 1011, a communication unit 1013, and a camera head control unit 1015. Furthermore, the input device 1047 includes a line-of-sight acquisition unit 2100 and a voice acquisition unit 2200 as its functions. The CCU 1039 includes, as functions thereof, a communication unit 1059, an image processing unit 1061, a control unit 1063, a line-of-sight information processing unit 2010, and a voice recognition unit 2020.

The camera head 1005 and the CCU 1039 are connected by a transmission cable 1065 so as to be bidirectionally communicable. In addition, the input device 1047 and the CCU 1039 are connected by a transmission cable 1066 so as to be bidirectionally communicable. Each of the transmission cables 1065 and 1066 is an electric signal cable compatible with electric signal communication, an optical fiber compatible with optical communication, or a composite cable thereof.

Note that, in the example of FIG. 2, communication is performed by wire using the transmission cables 1065 and 1066, but communication between the camera head 1005 and the CCU 1039 or communication between the input device 1047 and the CCU 1039 may be performed wirelessly. In a case where the communication between the two is performed wirelessly, it is not necessary to lay each of the transmission cables 1065 and 1066 in the operating room, so that a situation in which the movement of the medical staff in the operating room is hindered by each of the transmission cables 1065 and 1066 can be eliminated.

(Camera Head)

First, a functional configuration of the camera head 1005 will be described.

The lens unit 1007 is an optical system provided at a connection portion with the lens barrel 1003. Observation light taken in from the distal end of the lens barrel 1003 is guided to the camera head 1005 and enters the lens unit 1007. The lens unit 1007 is configured by combining a plurality of lenses including a zoom lens and a focus lens. The optical characteristics of the lens unit 1007 are adjusted so as to condense the observation light on the light receiving surface of the imaging element of the imaging unit 1009. Further, the zoom lens and the focus lens are configured to be movable in position on the optical axis in order to adjust the magnification and the focus of the captured image.

The imaging unit 1009 includes an imaging element and is arranged at a subsequent stage of the lens unit 1007. The observation light having passed through the lens unit 1007 is condensed on the light receiving surface of the imaging element, and an image signal corresponding to the observation image is generated by photoelectric conversion. The image signal generated by the imaging unit 1009 is provided to the communication unit 1013. Note that, as the imaging element constituting the imaging unit 1009, for example, a complementary metal oxide semiconductor (CMOS) type image sensor having a Bayer array and capable of color capturing is used. Note that, as the imaging element, for example, an imaging element that can cope with capturing of a high-resolution image of 4K or more may be used. By obtaining the image of the surgical site with high resolution, the operator 1067 can grasp the state of the surgical site in more detail, and can progress the surgery more smoothly.

The imaging unit 1009 images, for example, an operative field in the abdominal cavity (abdominal cavity environment). Specifically, the imaging unit 1009 acquires an operative field image including various medical instruments, organs, and the like in the abdominal cavity of the patient. The imaging unit 1009 is a camera or the like capable of capturing an image of a capturing target in the form of a moving image or a still image. Note that the imaging unit 1009 is not necessarily provided in the camera head 1005. For example, the imaging unit 1009 may be provided immediately after the objective lens inside the lens barrel 1003. Furthermore, the arm portion 1031 supports the camera head 1005, but is not limited thereto, and may support a medical instrument such as the forceps 1023, for example.

The endoscope 1001 having such an imaging unit 1009 may be, for example, a stereo endoscope, an oblique-viewing endoscope, a direct forward-viewing endoscope, or a wide-angle endoscope, and is not particularly limited. The angle of view of the wide-angle endoscope is, for example, 140°, but the angle of view may be smaller than 140° or may be 140° or more as long as it exceeds 80°. The stereo endoscope includes a pair of imaging elements for acquiring right-eye and left-eye image signals corresponding to 3D display. By performing the 3D display, the operator 1067 can more accurately grasp the depth of the living tissue in the surgical site. Note that, in a case where the imaging unit 1009 is configured as a multi-plate type, a plurality of systems of lens units 1007 is provided corresponding to each imaging element.

Furthermore, in addition to using a stereo endoscope capable of distance measurement as the endoscope 1001 including the imaging unit 1009, a depth sensor (distance measuring device) may be provided separately from the imaging unit 1009 using an endoscope other than the stereo endoscope. In this case, the imaging unit 1009 may be a monocular endoscope. The depth sensor may be, for example, a sensor that performs distance measurement using a time of flight (ToF) method in which distance measurement is performed using a return time of reflection of pulsed light from a subject, or a structured light method in which distance measurement is performed by distortion of a pattern by emitting lattice-shaped pattern light. Alternatively, the imaging unit 1009 itself may be provided with a depth sensor. In this case, the imaging unit 1009 can perform distance measurement by the ToF method simultaneously with imaging. Specifically, the imaging unit 1009 includes a plurality of light receiving elements, and can generate an image or calculate distance information on the basis of a pixel signal obtained from the light receiving elements.

The drive unit 1011 includes an actuator, and moves the zoom lens and the focus lens of the lens unit 1007 by a predetermined distance along the optical axis under the control of the camera head control unit 1015. As a result, the magnification and focus of the image captured by the imaging unit 1009 can be appropriately adjusted.

The communication unit 1013 includes a communication device for transmitting and receiving various types of information to and from the CCU 1039. The communication unit 1013 transmits the image signal obtained from the imaging unit 1009 as RAW data to the CCU 1039 via the transmission cable 1065. At this time, in order to display the captured image of the surgical site with low latency, the image signal is preferably transmitted by optical communication. This is because, at the time of surgery, the operator 1067 performs surgery while observing the state of the affected part with the captured image, and thus, for safer and more reliable surgery, it is required to display a moving image of the surgical site in real time as much as possible. In a case where optical communication is performed, the communication unit 1013 is provided with a photoelectric conversion module that converts an electric signal into an optical signal. The image signal is converted into an optical signal by the photoelectric conversion module and then transmitted to the CCU 1039 via the transmission cable 1065.

Furthermore, the communication unit 1013 receives a control signal for controlling driving of the camera head 1005 from the CCU 1039. The control signal includes, for example, information regarding imaging conditions such as information for designating a frame rate of a captured image, information for designating an exposure value at the time of imaging, and/or information for designating a magnification and a focus of a captured image. The communication unit 1013 provides the received control signal to the camera head control unit 1015. Note that the control signal from the CCU 1039 may also be transmitted by optical communication. In this case, the communication unit 1013 is provided with a photoelectric conversion module that converts an optical signal into an electric signal, and the control signal is converted into an electric signal by the photoelectric conversion module and then provided to the camera head control unit 1015.

Note that the imaging conditions such as the frame rate, the exposure value, the magnification, and the focus are automatically set by the control unit 1063 of the CCU 1039 on the basis of the acquired image signal. That is, the endoscope 1001 is equipped with a so-called auto exposure (AE) function, an auto focus (AF) function, and an auto white balance (AWB) function.

The camera head control unit 1015 controls driving of the camera head 1005 on the basis of the control signal from the CCU 1039 received via the communication unit 1013. For example, the camera head control unit 1015 controls driving of the imaging element of the imaging unit 1009 on the basis of the information to designate the frame rate of the captured image and/or the information to designate the exposure at the time of imaging. Furthermore, for example, the camera head control unit 1015 appropriately moves the zoom lens and the focus lens of the lens unit 1007 via the drive unit 1011 on the basis of the information to designate the magnification and the focus of the captured image. The camera head control unit 1015 may further have a function of storing information for identifying the lens barrel 1003 and the camera head 1005.

For example, the camera head control unit 1015 may control the enlargement magnification of the imaging unit 1009 on the basis of the input information received by the input device 1047, or may control the enlargement magnification of the imaging unit 1009 according to a state of an image captured by the imaging unit 1009, a state of display, or the like. Furthermore, the camera head control unit 1015 may control the focus (focal length) of the imaging unit 1009 or may control the gain (sensitivity) of the imaging unit 1009 (specifically, the image sensor of the imaging unit 1009) according to the state of the image captured by the imaging unit 1009, the state of display, and the like.

Note that by arranging the above-described configurations of the lens unit 1007, the imaging unit 1009, and the like in a sealed structure having high airtightness and waterproofness, the camera head 1005 can have resistance to autoclave sterilization.

(Input Device)

Next, a functional configuration of the input device 1047 will be described. The input device 1047 corresponds to an input unit.

The line-of-sight acquisition unit 2100 includes a communication unit 2101 and a line-of-sight detection unit 2102. The communication unit 2101 includes a communication device for transmitting and receiving various types of information to and from the CCU 1039. For example, the communication unit 2101 transmits the line-of-sight information regarding the line of sight detected by the line-of-sight detection unit 2102 to the CCU 1039. The line-of-sight detection unit 2102 detects the line of sight of the user such as the operator 1067. The line-of-sight detection unit 2102 is implemented by, for example, various cameras, a glasses-type wearable device, an HMD, or the like. The camera may be provided, for example, in the vicinity of the display device 1041. In addition, a glasses-type wearable device or an HMD is used by being worn by a user. Any device can detect the user's line of sight.

The voice acquisition unit 2200 includes a communication unit 2201 and a voice detection unit 2202. The communication unit 2201 includes a communication device for transmitting and receiving various types of information to and from the CCU 1039. For example, the communication unit 2201 transmits voice information regarding the voice detected by the voice detection unit 2202 to the CCU 1039. The voice detection unit 2202 detects the voice of the user such as the operator 1067. The voice detection unit 2202 is implemented by, for example, a microphone capable of collecting the voice of the user. The microphone may be provided, for example, in the vicinity of the display device 1041, or may be used by being worn by the user.

(CCU)

Next, a functional configuration of the CCU 1039 will be described.

The communication unit 1059 includes a communication device for transmitting and receiving various types of information to and from the camera head 1005 and the input device 1047. The communication unit 1059 transmits a control signal for controlling driving of the camera head 1005 to the camera head 1005. Furthermore, the communication unit 1059 receives an image signal transmitted from the camera head 1005 via the transmission cable 1065. Furthermore, the communication unit 1059 receives a line-of-sight signal and a voice signal (line-of-sight information and voice information) transmitted from the input device 1047 via the transmission cable 1066. The communication unit 1059 corresponds to a line-of-sight information acquisition unit or a voice information acquisition unit.

As described above, the communication unit 1059 preferably communicates the control signal, the image signal, the line-of-sight signal, the voice signal, and the like by optical communication. In this case, for optical communication, the communication unit 1059 is provided with a photoelectric conversion module that converts an optical signal into an electrical signal. The communication unit

1059 provides the control signal, the image signal, the line-of-sight signal, the voice signal, and the like converted into the electric signal to the image processing unit 1061, the control unit 1063, the line-of-sight information processing unit 2010, the voice recognition unit 2020, and the like.

The image processing unit 1061 performs various types of image processing on the image signal that is RAW data transmitted from the camera head 1005. Examples of the image processing include various known signal processing such as development processing, high image quality processing (band emphasis processing, super-resolution processing, noise reduction (NR) processing, camera shake correction processing, and/or the like), and/or enlargement processing (electronic zoom processing). Furthermore, the image processing unit 1061 performs detection processing on the image signal for performing AE, AF, and AWB.

For example, the image processing unit 1061 performs various types of image processing on the image signal obtained by the imaging unit 1009 of the camera head 1005, thereby generating image data related to the captured image. Furthermore, the image processing unit 1061 generates image data for output on the basis of the image data. The image data for output is, for example, image data processed into a format that can be processed by various data output devices such as the display device 1041, the recorder 1053, or the printer 1055 of the endoscopic surgery system 1000 described above.

Here, the captured image means an image having a magnification, an angle of view, a focus, and the like determined according to hardware of an imaging mechanism of the endoscope 1001, such as the imaging unit 1009 and an optical system provided in a preceding stage thereof. Meanwhile, the display image means an image actually displayed on the display device 1041. The display image may be the captured image itself. Alternatively, the display image may be an image obtained by subjecting the captured image to predetermined treatment, such as a partial region of the captured image cut out or a partial region of the captured image enlarged by the electronic zoom function. That is, the image processing unit 1061 generates image data related to the display image by performing various types of processing or without performing any processing on the image data related to the captured image.

Normally, during surgery, for what kind of display image the image processing unit 1061 generates image data can be appropriately set by the user. That is, at the normal time, the image processing unit 1061 generates image data related to the display image in accordance with conditions (for example, cutout of a captured image, enlargement by electronic zoom, and the like) appropriately set by the user. Then, the generated image data is transmitted to the display device 1041 and displayed. The operator 1067 operates instruments such as the energy treatment tool 1021 and the forceps 1023 while observing the state of the treatment part on the display image, and performs various treatments on the treatment part.

The line-of-sight information processing unit 2010 processes a line-of-sight signal (line-of-sight information) transmitted from the line-of-sight acquisition unit 2100 of the input device 1047 via the transmission cable 1066. For example, the line-of-sight information processing unit 2010 processes the line-of-sight signal and generates gaze information regarding a recognition result of the line of sight from the line-of-sight signal. Then, the line-of-sight information processing unit 2010 transmits the generated gaze information to the control unit 1063. The gaze information includes, for example, information such as the position and size of the line-of-sight retention region. The line-of-sight retention region is an example of the gaze region. Note that the line-of-sight information may be any information as long as a gaze point of the user can be detected, and may be a line of sight, a face direction, a body posture (for example, which direction the upper body is facing, and the like), a direction, a position, and a posture of the head, or the like. These directions and postures may be detected by, for example, an acceleration sensor. The line-of-sight information processing unit 2010 corresponds to a gaze information acquisition unit.

The voice recognition unit 2020 processes a voice signal (voice information) transmitted from the voice acquisition unit 2200 of the input device 1047 via the transmission cable 1066. For example, the voice recognition unit 2020 processes a voice signal, recognizes a voice from the voice signal, and generates recognition information regarding a recognition result of the voice. Then, the voice recognition unit 2020 transmits the generated voice recognition information to the control unit 1063. The voice recognition information includes, for example, information such as voice content.

The control unit 1063 performs various types of control related to imaging of the surgical site by the endoscope 1001 and display of the captured image. For example, the control unit 1063 generates a control signal for controlling driving of the camera head 1005. At this time, in a case where the imaging condition is input by the user, the control unit 1063 generates a control signal on the basis of the input by the user. Alternatively, in a case where the AE function, the AF function, and the AWB function are equipped for the endoscope 1001, the control unit 1063 appropriately calculates the optimum exposure value, focal length, and white balance according to the result of the detection processing by the image processing unit 1061, and generates a control signal. Furthermore, the control unit 1063 transmits the image data subjected to the image processing by the image processing unit 1061 to the display device 1041, and causes the display device 1041 to display a surgical site image based on the image data.

The control unit 1063 includes a target candidate recognition unit 2001, a reliability acquisition unit 2002, and a target determination unit 2003.

The target candidate recognition unit 2001 recognizes a tracking target candidate (candidate of tracking target object) from the operative field image (for example, a surgical site image) acquired by the imaging unit 1009. For example, the target candidate recognition unit 2001 recognizes various tracking target candidates in the operative field image from the image data related to the operative field image acquired by the imaging unit 1009 using various image recognition technologies (for example, machine learning or the like). The target candidate recognition unit 2001 can recognize various tracking target candidates, for example, instruments such as the forceps 1023 and tweezers, a specific living body site, and the like by detecting the shape, color, and the like of the edge of the object included in the surgical site image.

The reliability acquisition unit 2002 acquires the reliability of the recognition result of the tracking target candidate recognized by the target candidate recognition unit 2001, that is, the recognition reliability. For example, the reliability acquisition unit 2002 acquires the recognition reliability (for example, the estimation accuracy of the position of the tracking target candidate, the estimation accuracy of the type of the tracking target candidate, and the like) of each tracking target candidate.

The target determination unit 2003 determines a tracking target in the operative field image acquired by the imaging unit 1009 on the basis of the reliability information regarding the recognition reliability acquired by the reliability acquisition unit 2002. For example, in a case where there is a tracking target candidate whose recognition reliability is equal to or greater than a predetermined threshold, the target determination unit 2003 determines the tracking target candidate as a tracking target. The predetermined threshold is preset (it similarly applies to other thresholds described later).

On the other hand, in a case where there is no tracking target candidate whose recognition reliability is equal to or greater than the predetermined threshold, the target determination unit 2003 determines the tracking target candidate as the tracking target on the basis of the recognition information regarding the tracking target candidate recognized by the target candidate recognition unit 2001 and the gaze information regarding the gaze obtained by the line-of-sight information processing unit 2010. Note that the recognition information includes, for example, information regarding a recognition region of a tracking target candidate (for example, the position, size, and the like of the recognition region). The gaze information includes, for example, information (for example, the position, size, and the like of the retention region) regarding a line-of-sight retention region.

Here, each functional unit such as the communication unit 1059, the image processing unit 1061, the control unit 1063, the line-of-sight information processing unit 2010, and the voice recognition unit 2020 described above may be configured by both or either one of hardware and software. These configurations are not particularly limited. For example, each of the above-described functional units may be implemented by a computer such as a CPU or a micro processing unit (MPU) executing a program stored in advance in a ROM using a RAM or the like as a work area. Furthermore, each functional unit may be implemented by, for example, an integrated circuit such as an application specific integrated circuit (ASIC) or a field-programmable gate array (FPGA). The control unit 1063 corresponds to an information processing apparatus.

In such an endoscopic surgery system 1000, for example, the imaging unit 1009 is inserted into the body of the patient through a medical puncture device called a trocar 1025a, and the operator 1067 performs the laparoscopic surgery while imaging an area of interest. At this time, the imaging unit 1009 can freely change the imaging position by driving the arm portion 1031. Specifically, the endoscopic surgery system 1000 images the inside of the abdominal cavity of the patient by the imaging unit 1009, recognizes the environment in the abdominal cavity from the operative field image, and drives the arm portion 1031 on the basis of the recognition result of the environment in the abdominal cavity. By driving the arm portion 1031, the imaging range in the abdominal cavity changes. When the imaging range in the abdominal cavity changes, the endoscopic surgery system 1000 recognizes the changed environment and drives the arm portion 1031 on the basis of the recognition result. The endoscopic surgery system 1000 repeats image recognition of the environment in the abdominal cavity and driving of the arm portion 1031. That is, the endoscopic surgery system 1000 executes processing in which image recognition processing and processing of controlling the position and posture of the arm portion 1031 are fused.

Furthermore, the image processing unit 1061 acquires an image of the imaging target object captured by the imaging unit 1009, and generates various images on the basis of the image captured by the imaging unit 1009. Specifically, the image processing unit 1061 can generate an image by cutting out and enlarging a display target region (cutout range) in the image captured by the imaging unit 1009. For example, the image processing unit 1061 may change the display target region (cutout range), that is, the position where the image is cut out, according to the state of the image captured by the imaging unit 1009, the state of display, and the like. Note that the display target region may be designated by a user such as a doctor or an assistant using the input device 1047, or may be determined on the basis of an image recognition result, for example.

Note that, in the endoscopic surgery system 1000, the electronic degree of freedom of changing the line of sight by cutting out the image captured by the imaging unit 1009 and the degree of freedom by the actuator of the arm portion 1031 can be all treated as the degrees of freedom of the robot. As a result, it is possible to implement motion control in which an electronic degree of freedom for changing the line of sight and a degree of freedom by the actuator are linked.

In such an endoscopic surgery system 1000, the tracking control is performed such that the tracking target determined by the target determination unit 2003 is positioned in the operative field image, for example, positioned at the center of the operative field image. As the tracking control, the arm control device 1045 may control the arm portion 1031 so that the tracking target determined by the target determination unit 2003 is positioned in the operative field image. Alternatively, as the tracking control, the image processing unit 1061 may generate the operative field image such that the tracking target determined by the target determination unit 2003 is positioned in the operative field image. For example, the image processing unit 1061 may change the display target region (cutout range) such that the tracking target is positioned in the operative field image. One or both of these tracking controls are appropriately executed.

An example of the endoscopic surgery system 1000 to which the technology according to the present disclosure can be applied has been described above. Note that, here, the endoscopic surgery system 1000 has been described as an example, but the system to which the technology according to the present disclosure can be applied is not limited to such an example. For example, the technology according to the present disclosure may be applied to a flexible endoscopic surgery system for examination or a microscopic surgery system.

1-2. Processing Example Related to Tracking Target Determination

1-2-1. First Processing Example

Figure 3:
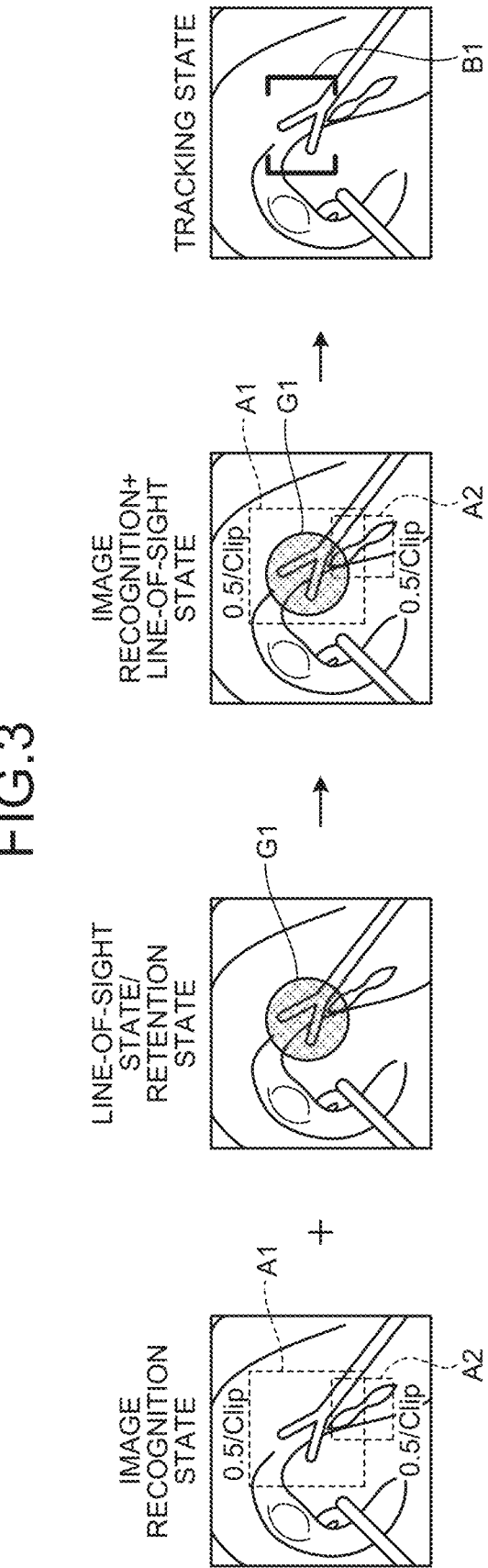
FIG. 3 is a diagram for explaining a first processing example according to an embodiment of the present disclosure.

A first processing example according to the present embodiment will be described with reference to FIG. 3. FIG. 3 is a diagram for explaining a first processing example according to the present embodiment. A first processing example is a processing example of image recognition and tracking target determination based on line-of-sight information. In the first processing example, in a case where the tracking target cannot be uniquely narrowed down from the recognition information, the tracking target (automatic tracking target) is determined from a plurality of tracking target candidates using both the recognition information and the line-of-sight information.

As illustrated in FIG. 3, in the image recognition state, the recognition area A1 and the recognition area A2 of the image recognition result exist in the operative field image being displayed. Each of the recognition target objects in the recognition areas A1 and A2 is a tracking target candidate. In the example of FIG. 3, the tracking target candidate in the recognition area A1 is the distal end portion of the instrument (for example, forceps 1023), and the tracking target candidate in the recognition area A2 is not the instrument but the glossy portion of erroneous recognition. Each of these recognition areas A1 and A2 is a recognition region (for example, a bounding box) surrounding a recognition target object, and is set by the target candidate recognition unit 2001.

At this time, the recognition reliability that is the reliability of image recognition is obtained by the reliability acquisition unit 2002. Examples of the recognition reliability include estimation accuracy of the position of the recognition target object (tracking target candidate) in the XY direction, estimation accuracy of the position of the recognition target object in the Z direction, and estimation accuracy of the type of the recognition target object. The position in the XY direction is a position in a plane, and the position in the Z direction is a position in a depth direction orthogonal to the plane.

Here, the recognition reliability is a probability indicating whether or not a recognition target object such as an instrument is included in a bounding box of a target, that is, a probability indicating whether or not the recognition target object is accurately captured in a region of the bounding box. This recognition reliability is obtained in association with the recognition information that is the image recognition result. The recognition reliability is defined in a range of 0 to 1, for example, and increases as the numerical value increases. In the example of FIG. 3, the recognition reliability of the recognition area A1 is 0.5, and the recognition reliability of the recognition area A2 is also 0.5. For example, when a predetermined threshold at which the recognition reliability passes is set to 0.9, the recognition reliability of both the recognition area A1 and the recognition area A2 is low.

In the line-of-sight state/retention state, a line-of-sight retention area (gaze area) G1 exists in the operative field image being displayed. The line-of-sight retention area G1 is determined by the line-of-sight information processing unit 2010 based on determination of a region where the line of sight is retained from the line-of-sight information. As a result, gaze information regarding the gaze of the user is obtained. The line-of-sight information includes a line-of-sight position projected on the screen on which the operative field image is displayed. In the example of FIG. 3, the user is looking at the distal end portion of the instrument, and the line of sight is retained at the distal end portion of the instrument. Such line-of-sight positions may be averaged in time series.

Here, the line-of-sight retention state is an example of a gaze state. Regarding this gaze state, for example, a state in which the retention time of the line of sight exceeds a certain value is the "gaze state". The retention time may be appropriately set, and different retention times may be set for different recognition targets. Furthermore, different retention times may be set according to the nature of the recognition target, such as a case where the recognition target is a character or a case where the recognition target is moving such as forceps.

In the image recognition+line-of-sight state, the recognition area A1, the recognition area A2, and the line-of-sight retention area G1 are recognized, and one of the tracking target candidates of the recognition area A1 and the recognition area A2 is determined as a tracking target by the target determination unit 2003 according to the overlapping area between the line-of-sight retention area G1 and the recognition area A1 or the recognition area A2 (matching degree between the line-of-sight retention area G1 and the image recognition result). In the example of FIG. 3, since the area of the region where the line-of-sight retention area G1 and the recognition area A1 overlap is equal to or larger than a predetermined threshold (for example, 80%) and is larger than the area of the region where the line-of-sight retention area G1 and the recognition area A2 overlap, a tracking target candidate in the recognition area A1, for example, a distal end portion of an instrument is determined as a tracking target.

In the tracking state, a tracking operation, that is, tracking control is executed on the basis of the tracking target in the recognition area A1. This tracking control is executed such that the determined tracking target is positioned in the central region in the screen. For example, it is desirable that the tracking control is executed such that the distal end portion of the instrument as the tracking target is positioned at the center of the screen, but the present invention is not limited thereto. At least the tracking control is only required to be executed so that the region of interest such as the distal end portion of the instrument is positioned in the screen.

According to such a first processing example, one tracking target is determined from a plurality of tracking target candidates using both the recognition information and the line-of-sight information (more specifically, gaze information based on the line-of-sight information). As a result, cooperation between the autonomous system and the user intention can be implemented, and the automatic tracking accuracy with respect to the tracking target can be improved even in a situation where the image recognition cannot be performed well (even if the recognition reliability becomes low). Here, in the image recognition based surgical instrument automatic tracking (for example, a target, a position, a speed, and the like), in a situation where the image recognition cannot be performed well, an operation (for example, different instrument types, positions, zoom ratios, and the like) different from expectation may occur. At this time, as a result, deviation of the field of view or the like occurs, and the surgeon needs to perform manual adjustment, so that an efficient procedure is hindered. However, according to the first processing example, even in a situation where image recognition cannot be performed well, one tracking target is determined from a plurality of tracking target candidates, so that it is possible to reduce the burden on the doctor and improve the accuracy of automatic tracking.

Here, in a case where the number of tracking target candidates is one from the beginning and the recognition reliability is a predetermined threshold (for example, 0.9) or more, the first processing example may not be executed and the one tracking target candidate may be determined as a tracking target. Furthermore, in a case where there is a plurality of tracking target candidates whose recognition reliability is equal to or greater than a predetermined threshold, the first processing example may not be executed, and for example, a tracking target candidate having the highest recognition reliability may be determined as a tracking target. In addition, the process of determining the tracking target according to the recognition reliability and the first processing example may be executed in combination.

Note that, in the example of FIG. 3, the mark B1 (for example, square brackets) indicating the tracking target may be superimposed and displayed on the operative field image, or may not be displayed. The display and non-display of the mark B1 can be switched by the user. The user operates the input device 1047 to input a switching instruction. In a case where the mark B1 is displayed, the user can accurately grasp the tracking target. On the other hand, in a case where the mark B1 is not displayed, it is possible to visually recognize a portion where the mark B1 overlaps the operative field image and becomes invisible, so that the operation can be accurately performed. In this manner, the user can appropriately select display and non-display of the mark B1, so that the convenience of the user can be improved.

Furthermore, the marks (for example, a dotted line or a solid line) indicating the recognition area A1, the recognition area A2, the line-of-sight retention area G1, and the like are not normally displayed, but are not limited thereto, and may be superimposed and displayed on the operative field image. In a case where a mark indicating the recognition area A1, the recognition area A2, or the like is displayed, the user can accurately grasp the tracking target candidate. Furthermore, in a case where a mark indicating the line-of-sight retention area G1 is displayed, the user can accurately grasp the position of the line of sight. On the other hand, in a case where the mark is not displayed, it is possible to visually recognize a portion where the mark overlaps the operative field image and is invisible, so that the operation can be accurately performed. As described above, similarly to the above, the user can appropriately select the display and non-display of the mark, so that the convenience of the user can be improved.

1-2-2. Second Processing Example

Figure 4:
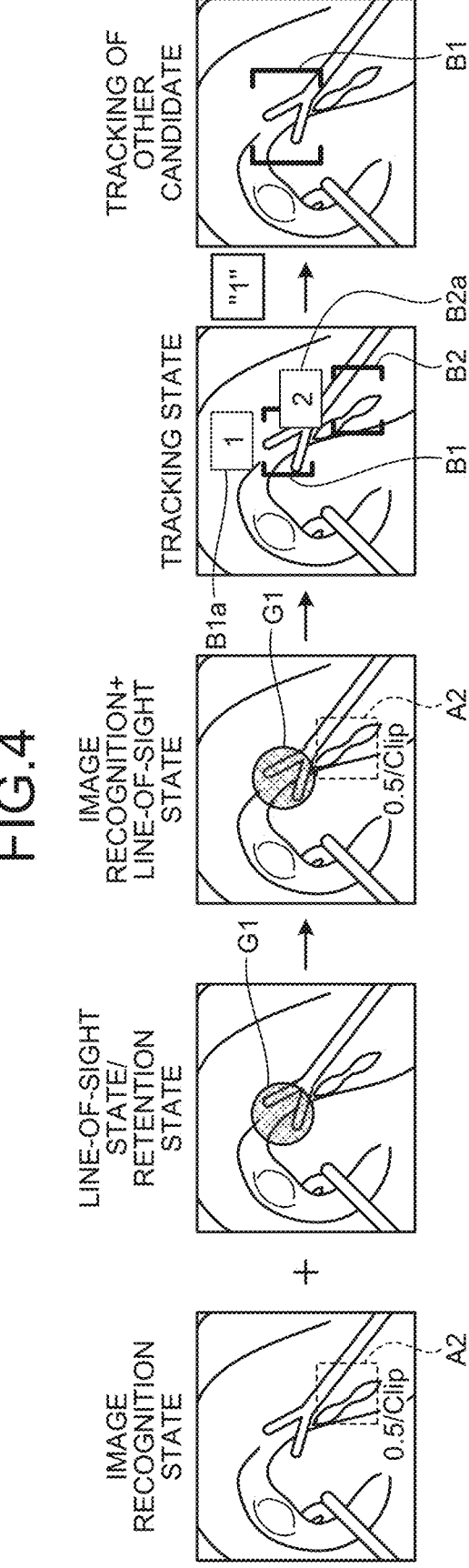
FIG. 4 is a diagram for explaining a second processing example according to an embodiment of the present disclosure.

A second processing example according to the present embodiment will be described with reference to FIG. 4. FIG. 4 is a diagram for explaining a second processing example according to the present embodiment. The second processing example is a processing example of tracking target determination by image recognition, line-of-sight information, and voice information. In the second processing example, in a case where the tracking target cannot be uniquely narrowed down even if the recognition information and the line-of-sight information are used in combination, the tracking target is determined from a plurality of tracking target candidates by using the voice information in combination with the recognition information and the line-of-sight information.

As illustrated in FIG. 4, in the image recognition state, the recognition area A2 of the image recognition result exists in the operative field image being displayed. As a result, there is one tracking target candidate. In the example of FIG. 4, the tracking target candidate in the recognition area A2 is not an instrument but a glossy portion of erroneous recognition, and the distal end portion of the instrument is not recognized. Similarly to the first processing example, the recognition area A2 is set by the target candidate recognition unit 2001, and the recognition reliability is obtained by the reliability acquisition unit 2002.

In the line-of-sight state/retention state, similarly to FIG. 3, a line-of-sight retention area (gaze area) G1 exists in the operative field image being displayed. Similarly to the first processing example, in the line-of-sight retention area G1, a region in which the line of sight is retained is determined from the line-of-sight information by the line-of-sight information processing unit 2010. As a result, gaze information regarding the gaze of the user is obtained. In the example of FIG. 4, the user is looking at the distal end portion of the instrument, and the line of sight is retained at the distal end portion of the instrument.

In the image recognition+line-of-sight state, the recognition area A2 and the line-of-sight retention area G1 are recognized, and the overlapping area between the line-of-sight retention area G1 and the recognition area A2 (the matching degree between the line-of-sight retention area G1 and the image recognition result) is obtained by the target determination unit 2003. In the example of FIG. 4, the line-of-sight retention area G1 and the recognition area A2 do not overlap, and the area of the region where the line-of-sight retention area G1 and the recognition area A2 overlap is 0 (zero). For this reason, the tracking target candidate in the recognition area A2 is not determined as the tracking target, and in addition to the tracking target candidate in the recognition area A2, the recognition target object in the line-of-sight retention area G1 is recognized by the target candidate recognition unit 2001 and set as the tracking target candidate.

In the tracking state, the target determination unit 2003 determines which of the tracking target candidates in the line-of-sight retention area G1 and the recognition area A2 is the tracking target on the basis of the voice information of the user. The voice of the user is detected by the voice detection unit 2202 and recognized by the voice recognition unit 2020. On the basis of the voice recognition information regarding the voice recognition result, one of the tracking target candidates in the line-of-sight retention area G1 and the recognition area A2 is determined as a tracking target.

In the example of FIG. 4, two marks B1 and B2 (for example, square brackets) are superimposed and displayed on the operative field image, and a number (for example, 1 or 2) for identifying each of the marks B1 and B2 is also superimposed and displayed on the operative field image. Each of the marks B1 and B2 is illustrated so as to surround the tracking target candidate. The user visually recognizes the display image, emits "1", and selects a tracking target candidate. The voice is detected by the voice detection unit 2202 and recognized by the voice recognition unit 2020. On the basis of the voice recognition information, a tracking target candidate corresponding to "1", that is, the distal end portion of the instrument is determined as a tracking target. That is, the tracking target candidate in the line-of-sight retention area G1 is determined as the tracking target.

In the tracking of the other candidate, a tracking operation, that is, tracking control is executed on the basis of a tracking target in the line-of-sight retention area G1. This tracking control is executed such that the determined tracking target is positioned in the central region in the screen. For example, it is desirable that the tracking control is executed such that the distal end portion of the instrument as the tracking target is positioned at the center of the screen, but the present invention is not limited thereto. Similarly to the first processing example, the tracking control is only required to be executed so that at least the region of interest such as the distal end portion of the instrument is positioned in the screen.

According to such a second processing example, even in a case where the tracking target cannot be uniquely narrowed down by using both the recognition information and the line-of-sight information (more specifically, gaze information based on the line-of-sight information), the tracking target can be easily determined by the intervention of the user. As a result, even in a situation where the image recognition cannot be performed well, the automatic tracking accuracy with respect to the tracking target can be improved.

Note that, in the example of FIG. 4, each of the marks B1 and B2 is superimposed and displayed on the operative field image, but the present invention is not limited thereto, and may not be displayed similarly to the first processing example. Furthermore, a mark (for example, a dotted line or a solid line) indicating the recognition area A2, the line-of-sight retention area G1, and the like is not normally displayed, but is not limited thereto, and may be superimposed and displayed on the operative field image.

In addition, a number (for example, 1 or 2) is superimposed and displayed on the operative field image in order to identify each of the marks B1 and B2. However, characters, symbols, and the like may be displayed instead of the number, or the numbers, characters, symbols, and the like may be displayed in combination.

1-2-3. Third Processing Example

A third processing example according to the present embodiment will be described with reference to FIG. 5. FIG. 5 is a diagram for explaining a third processing example according to the present embodiment. The third processing example is a processing example of tracking target determination by image recognition, line-of-sight information, and voice information. In the third processing example, the tracking target determined by using both the recognition information and the line-of-sight information is changed on the basis of the voice information.

As illustrated in FIG. 5, in the image recognition state, similarly to FIG. 3, the recognition area A1 and the recognition area A2 of the image recognition result exist in the operative field image being displayed. Each of the recognition target objects in the recognition areas A1 and A2 is a tracking target candidate. In the example of FIG. 5, similarly to FIG. 3, the tracking target candidate in the recognition area A1 is the distal end portion of the instrument (for example, forceps 1023), and the tracking target candidate in the recognition area A2 is not the instrument but the glossy portion of erroneous recognition.

In the line-of-sight state/retention state, similarly to FIG. 3, a line-of-sight retention area (gaze area) G1 exists in the operative field image being displayed. The line-of-sight retention area G1 is determined by the line-of-sight information processing unit 2010 based on determination of a region where the line of sight is retained from the line information. As a result, gaze information regarding the gaze of the user is obtained. In the example of FIG. 5, the user looks at a portion close to the distal end of the instrument or a glossy portion, and the line of sight is retained at the portion close to the distal end of the instrument or the glossy portion.

In the image recognition+line-of-sight state, similarly to FIG. 3, the recognition area A1, the recognition area A2, and the line-of-sight retention area G1 are recognized, and one of the tracking target candidates of the recognition area A1 and the recognition area A2 is determined as a tracking target by the target determination unit 2003 according to the overlapping area between the line-of-sight retention area G1 and the recognition area A1 or the recognition area A2 (matching degree between the line-of-sight retention area G1 and the image recognition result). In the example of FIG. 5, the area of the region where the line-of-sight retention area G1 and the recognition area A1 overlap is equal to or larger than a predetermined threshold (for example, 80%), but is smaller than the area of the region where the line-of-sight retention area G1 and the recognition area A2 overlap. Therefore, a tracking target candidate, for example, a glossy portion, in the recognition area A2 is determined as a tracking target.

In the tracking state, the target determination unit 2003 changes the tracking target once determined on the basis of the voice information of the user. The voice of the user is detected by the voice detection unit 2202 and recognized by the voice recognition unit 2020. Alternatively, the instrument operation by the user is recognized by the target candidate recognition unit 2001. On the basis of the voice recognition information regarding the voice recognition result or the operation information regarding the instrument operation, another tracking target candidate is determined as the tracking target.

In the example of FIG. 5, the mark B1 (for example, square brackets) is displayed to be superimposed on the operative field image. The user visually recognizes the display image and emits "not there", and sets another tracking target candidate as a tracking target. The voice is detected by the voice detection unit 2202 and recognized by the voice recognition unit 2020. On the basis of the voice recognition information regarding the voice recognition result, another tracking target candidate, that is, the distal end portion of the instrument is determined as the tracking target. Alternatively, the user operates an instrument (for example, forceps 1023) to open and close the distal end portion of the instrument twice, and sets another tracking target candidate as a tracking target. The two opening/ closing operations are recognized by the target candidate recognition unit 2001, and another tracking target candidate, that is, the distal end portion of the instrument is determined as the tracking target on the basis of the image recognition result, that is, the operation information regarding the instrument operation.

In the tracking of the other candidate, a tracking operation, that is, tracking control is executed on the basis of a tracking target in the recognition area A1. This tracking control is executed such that the determined tracking target is positioned in the central region in the screen. For example, it is desirable that the tracking control is executed such that the distal end portion of the instrument as the tracking target is positioned at the center of the screen, but the present invention is not limited thereto. Similarly to the other processing examples, the tracking control is only required to be executed such that at least the region of interest such as the distal end portion of the instrument is positioned in the screen.

According to such a third processing example, the tracking target determined by using the recognition information and the line-of-sight information (more specifically, gaze information based on the line-of-sight information) in combination can be easily changed by the intervention of the user. As a result, even in a situation where the image recognition cannot be performed well, the automatic tracking accuracy with respect to the tracking target can be improved. In addition, since the change can be made by voice or instrument operation, the change operation is easy, and the convenience of the user can be improved.

Note that, in the example of FIG. 5, the mark B1 is superimposed and displayed on the operative field image, but the present invention is not limited thereto. For example, the mark B1 may not be displayed similarly to the other processing examples except for the timing at which the user selects the tracking target. Furthermore, the marks (for example, a dotted line or a solid line) indicating the recognition area A1, the recognition area A2, the line-of-sight retention area G1, and the like are not normally displayed, but are not limited thereto, and may be superimposed and displayed on the operative field image.

In addition, the voice content for changing the tracking target may be words other than "not there", and the number of opening/closing operations of the instrument for changing the tracking target may be one or three or more, and the number is not limited. In addition, the instrument operation may be other than the opening/closing operation, and may be, for example, an operation of swinging the instrument to the left and right several times. In addition, the gesture for changing the tracking target may be other than the instrument operation.

1-2-4. Fourth Processing Example

Figure 6:
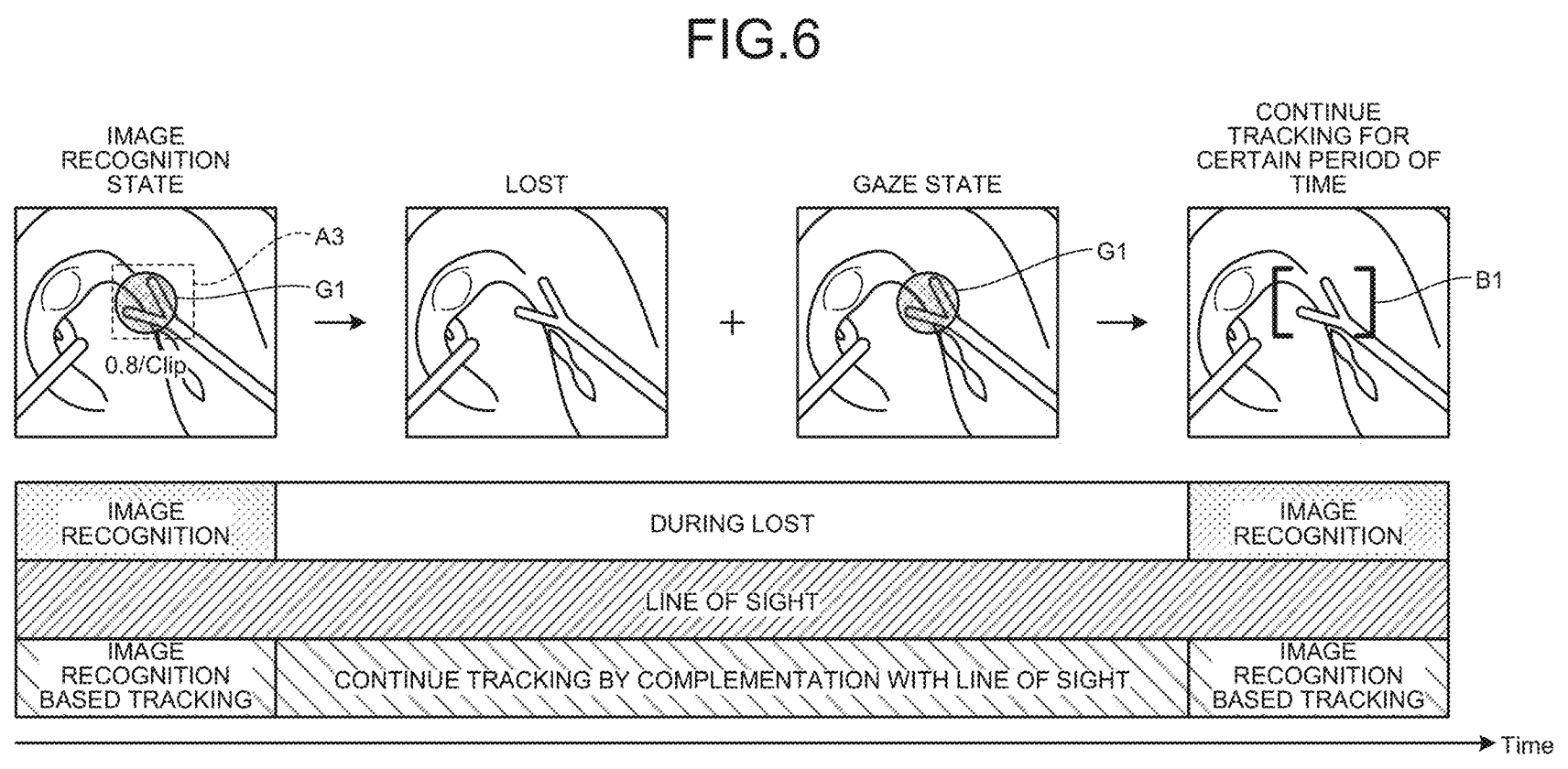

A fourth processing example according to the present embodiment will be described with reference to FIG. 6. FIG. 6 is a diagram for explaining a fourth processing example according to the present embodiment. A fourth processing example is a tracking complement processing example. In the fourth processing example, in a case where the image recognition cannot be performed halfway, the tracking target is captured using the line-of-sight information to complement the lost period.

As illustrated in FIG. 6, in the image recognition state, image recognition based tracking based on image confirmation and line-of-sight information is executed. At this time, the tracking target is determined by any one of the first to third processing examples described above. In the example of FIG. 6, a recognition area A3 of the image recognition result exists in the operative field image being displayed, and a line-of-sight retention area (gaze area) G1 exists. The recognition reliability of the recognition area A3 is 0.8.

In the loss, the tracking target is not recognized by the image recognition for some reason. In the gaze state, line-of-sight based tracking based on the line-of-sight information is executed. During this lost period, tracking is continued by complementation with a line of sight. That is, during the lost period, the tracking control is executed on the basis of the line-of-sight information.

After the tracking is continued for a certain period of time, when the tracking target is recognized again by image recognition, image recognition based tracking based on image confirmation and line-of-sight information is executed. On the other hand, in a case where the tracking target is not recognized even if the tracking is continued for a certain period of time, for example, error display indicating that the tracking target has completely lost is executed.

According to such a fourth processing example, even if the tracking target is not recognized by the image recognition and a loss occurs, the tracking target is tracked on the basis of the line-of-sight information. As a result, even if the loss occurs, the automatic tracking can be continued, so that the provision of the operative field image desired by the user can be continued.

1-2-5. Fifth Processing Example

Figure 7:
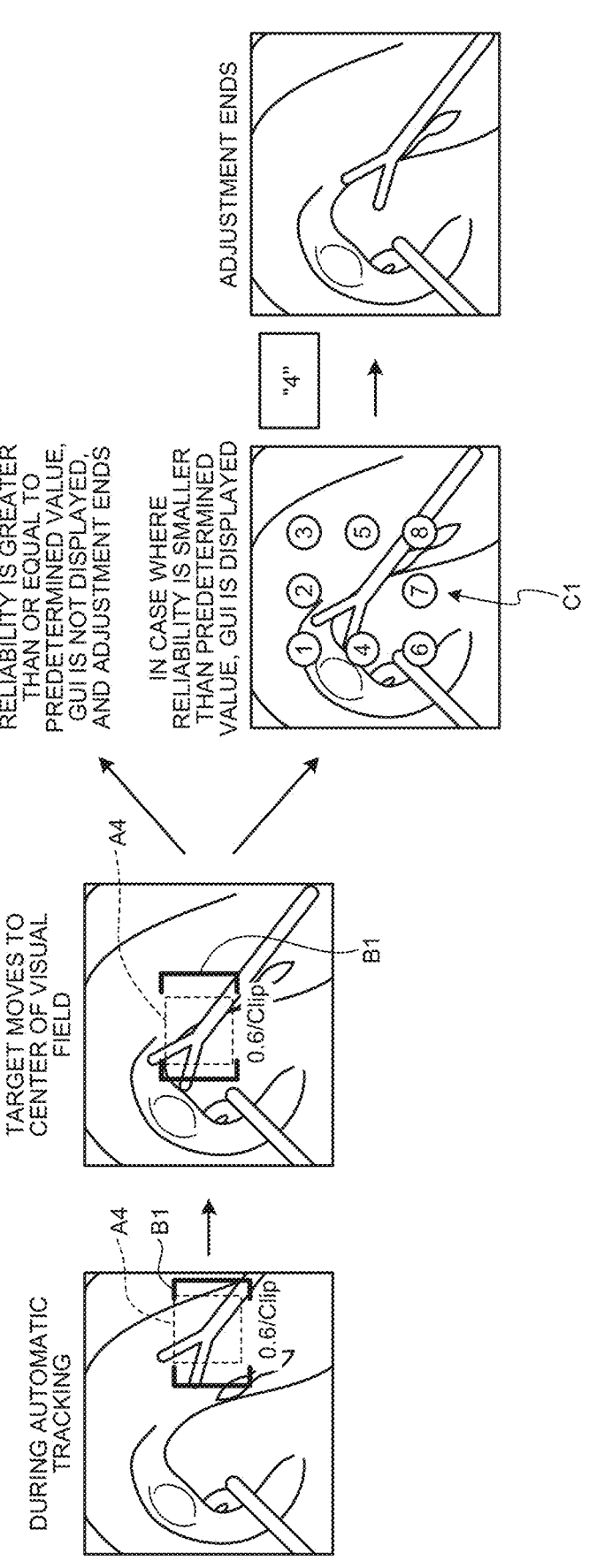
FIG. 7 is a diagram for explaining a fifth processing example according to an embodiment of the present disclosure.

A fifth processing example according to the present embodiment will be described with reference to FIG. 7. FIG. 7 is a diagram for explaining a fifth processing example according to the present embodiment. The fifth processing example is a processing example of position adjustment in the XY direction (planar direction). In the fifth processing example, display/non-display of a position adjustment graphical user interface (GUI) is determined from the recognition reliability in the XY directions, and easy user adjustment is enabled in a case where adjustment is necessary.

As illustrated in FIG. 7, during automatic tracking, a tracking target is recognized by image recognition. The tracking target is determined by any one of the first to third processing examples described above, for example. In the example of FIG. 7, the recognition area A4 of the image recognition result exists in the operative field image being displayed, and the recognition reliability of the recognition area A4 is 0.6. Note that the mark B1 may be superimposed and displayed on the operative field image.

In the tracking control, for example, the tracking control is performed such that the tracking target moves to the center of the visual field (the center of the operative field image). In a case where the recognition reliability is greater than or equal to a predetermined value (predetermined threshold), the position adjustment GUI is not displayed, and the tracking adjustment ends. On the other hand, in a case where the recognition reliability is smaller than the predetermined value, the position adjustment GUI, that is, the position adjustment image C1 is superimposed and displayed on the operative field image. The position adjustment image C1 is an image for the user to adjust the position of the tracking target in the XY direction. For example, the position adjustment image C1 is generated by the image processing unit 1061.

In the example of FIG. 7, the position adjustment image C1 is an image for the user to designate a position for centering the tracking target in the operative field image. In the position adjustment image C1, a plurality of numbers (for example, 1 to 8) is arranged in a square shape. When the user designates a number by voice, the operative field image is adjusted by the image processing unit 1061 such that the position of the number becomes the center of the operative field image.

For example, the user visually recognizes the display image, emits "4", and selects a desired position. The voice is detected by the voice detection unit 2202 and recognized by the voice recognition unit 2020. The operative field image is adjusted by the image processing unit 1061 such that the position of "4" is the center position of the operative field image, and the adjusted operative field image is displayed by the display device 1041. Note that, at a predetermined timing after the number is selected, the position adjustment image C1 is no longer displayed, and the tracking adjustment ends. The predetermined timing may be a timing after a predetermined time from the completion of the number selection, or may be a timing instructed by an input operation by the user.

According to such a fifth processing example, in a case where the user feels that the position adjustment in the XY direction (planar direction) is necessary, the position adjustment in the XY direction can be easily performed using the position adjustment image C1 functioning as the position adjustment GUI. As a result, the provision of the operative field image desired by the user can be continued.

1-2-6. Sixth Processing Example

Figure 8:
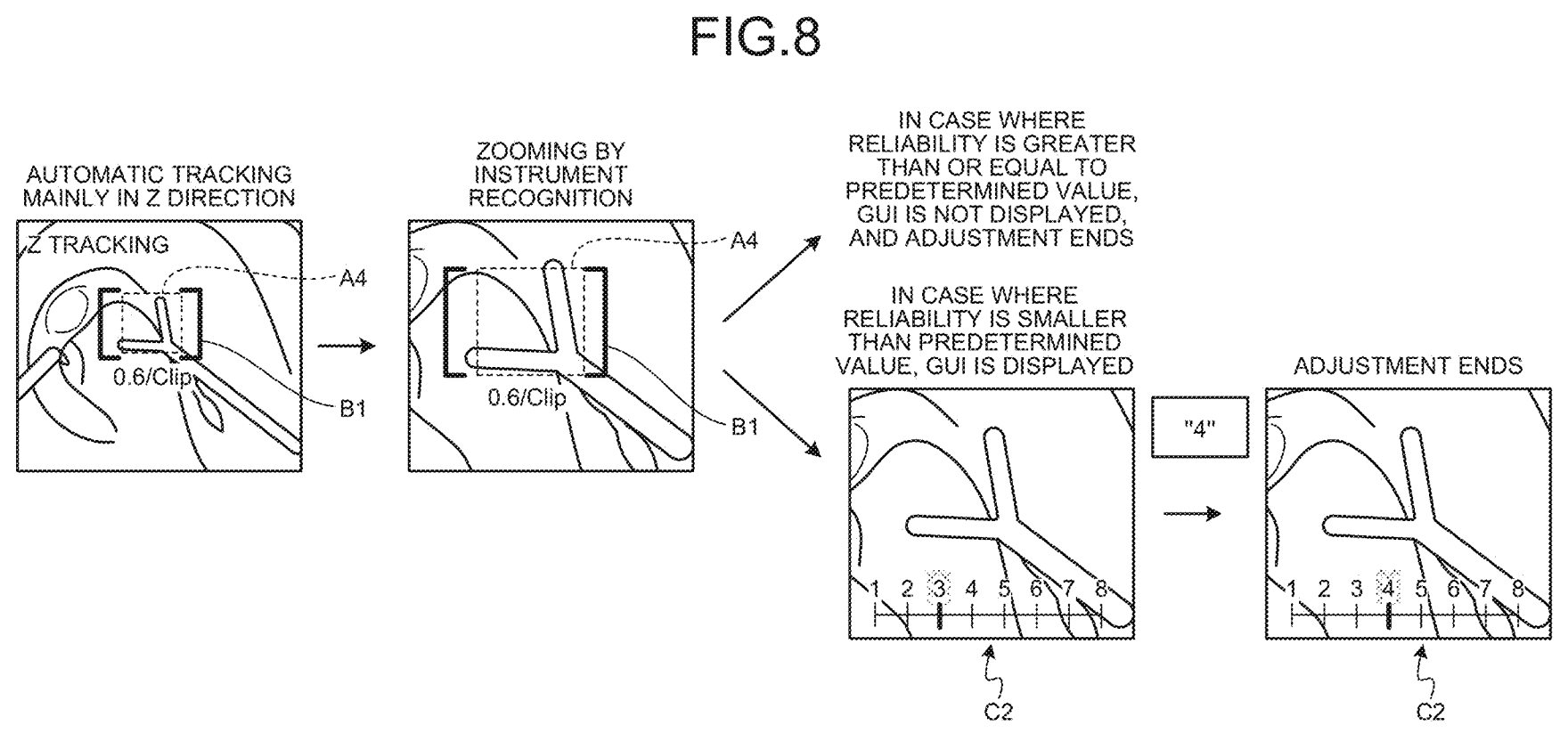

A sixth processing example according to the present embodiment will be described with reference to FIG. 8. FIG. 8 is a diagram for explaining a sixth processing example according to the present embodiment. The sixth processing example is a processing example of position adjustment in the Z direction (depth direction). In the sixth processing example, display/non-display of the zoom adjustment GUI is determined from the recognition reliability in the Z direction, and easy user adjustment is enabled in a case where adjustment is necessary.

As illustrated in FIG. 8, during automatic tracking mainly in the Z direction, a tracking target is recognized by image recognition similarly to FIG. 7. The tracking target is determined by any one of the first to third processing examples described above, for example. In the example of FIG. 8, similarly to FIG. 7, the recognition area A4 of the image recognition result exists in the operative field image being displayed, and the recognition reliability of the recognition area A4 is 0.6. Note that the mark B1 may be superimposed and displayed on the operative field image.

In the zooming by the instrument recognition, when the zooming is executed, the tracking target is enlarged. For example, the user operates the input device 1047 to instruct zooming. In a case where the recognition reliability is greater than or equal to a predetermined value (predetermined threshold), the zoom adjustment GUI is not displayed, and the tracking adjustment ends. On the other hand, in a case where the recognition reliability is smaller than the predetermined value, the zoom adjustment GUI, that is, the position adjustment image C2 is superimposed and displayed on the operative field image. The position adjustment image C2 is an image for the user to adjust the position of the tracking target in the Z direction. For example, the position adjustment image C2 is generated by the image processing unit 1061.

In the example of FIG. 8, the position adjustment image C2 is an image for the user to designate the position of the tracking target in the Z direction, that is, the position in the depth direction. In the position adjustment image C2, linear graduations are arranged, and the numerical value of the graduations is, for example, 1 to 8. When the user designates a number by voice, zooming is performed to a position in the depth direction corresponding to the position of the number, and the operative field image is adjusted by the image processing unit 1061.

For example, the user visually recognizes the display image, emits "4", and selects a desired position. The voice is detected by the voice detection unit 2202 and recognized by the voice recognition unit 2020. The operative field image is adjusted by the image processing unit 1061 so that the zoom matches the depth position based on the position of "4", and the adjusted operative field image is displayed by the display device 1041. Note that, at a predetermined timing after the number is selected, the position adjustment image C2 is no longer displayed, and the tracking adjustment ends. The predetermined timing may be a timing after a predetermined time from the completion of the number selection, or may be a timing instructed by an input operation by the user.

According to such a sixth processing example, in a case where the user feels that the position adjustment in the Z direction (depth direction) is necessary, the position adjustment in the Z direction can be easily performed using the position adjustment image C2 functioning as the zoom adjustment GUI. As a result, the provision of the operative field image desired by the user can be continued.

1-2-7. Seventh Processing Example

Figure 9:
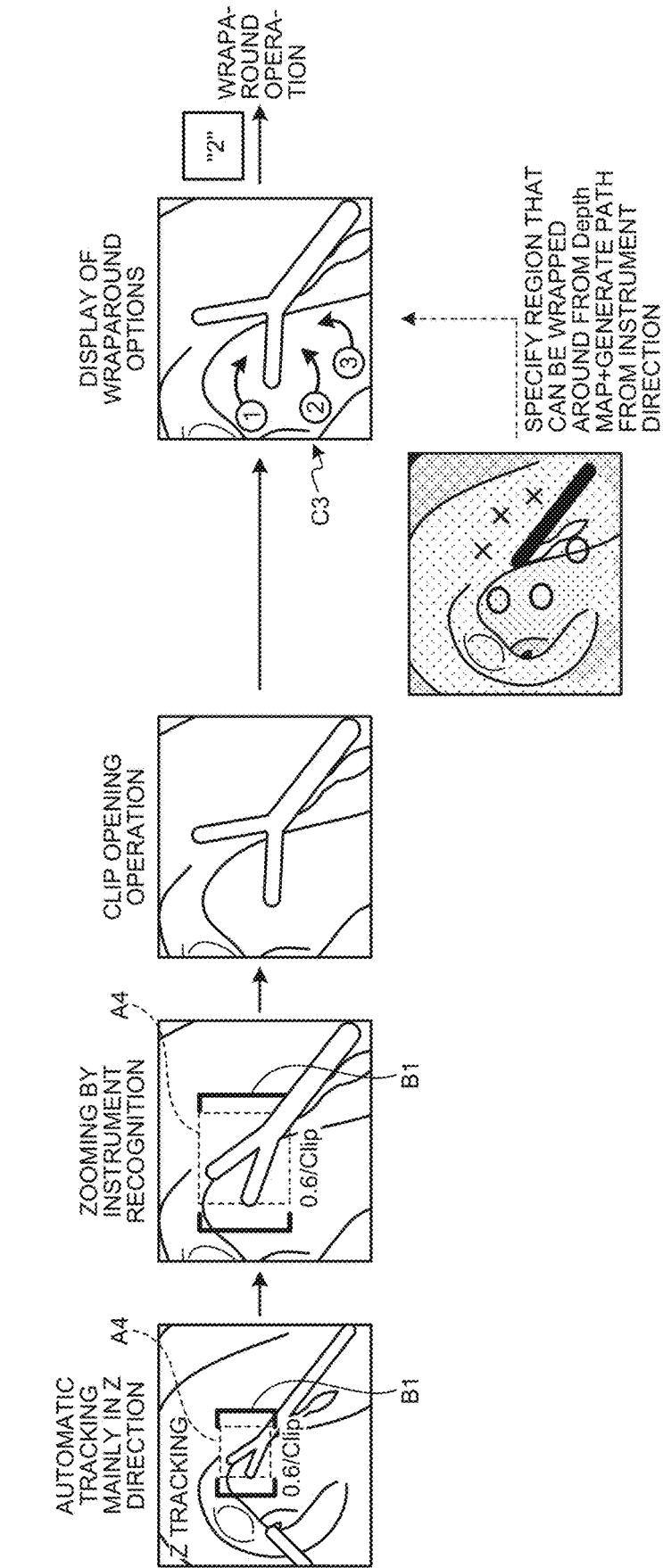
FIG. 9 is a diagram for explaining a seventh processing example according to an embodiment of the present disclosure.

A seventh processing example according to the present embodiment will be described with reference to FIG. 9. FIG. 9 is a diagram for explaining a seventh processing example according to the present embodiment. A seventh processing example is a processing example of camerawork selection. In the seventh processing example, in a case where special camerawork (for example, wraparound or the like) is required, a wraparound path is generated from the depth information, and a path selection GUI is displayed to enable user selection.

As illustrated in FIG. 9, during automatic tracking mainly in the Z direction, a tracking target is recognized by image recognition similarly to FIG. 8. The tracking target is determined by any one of the first to third processing examples described above, for example. In the example of FIG. 9, similarly to FIG. 8, the recognition area A4 of the image recognition result exists in the operative field image being displayed, and the recognition reliability of the recognition area A4 is 0.6. Note that the mark B1 may be superimposed and displayed on the operative field image.

In the zooming by the instrument recognition, when the zooming is executed, the tracking target is enlarged. For example, the user operates the input device 1047 to instruct zooming. Further, the user operates the instrument (for example, forceps 1023) to perform an operation of opening the distal end portion (clip) of the instrument. This serves as a trigger, and the path selection GUI indicating the wraparound option, that is, the path selection image C3 is displayed to be superimposed on the operative field image. The path selection image C3 is an image for the user to select a desired path from a plurality of paths. For example, the path selection image C3 is generated by the image processing unit 1061.

In the example of FIG. 9, the path selection image C3 is an image indicating a plurality of wraparound paths that can be selected. In the path selection image C3, the wraparound paths are indicated by arrows, and numbers (for example, 1 to 3) for identifying these paths are added. Note that, in each wraparound path, a region that can be wrapped around is specified by the image processing unit 1061 from the depth map information (for example, depth information or the like having a depth to the portion for each of all coordinate points of the XY coordinates) in the lower diagram, and is determined from the direction of the instrument on the basis of the specified region. A mark "x" in the lower diagram indicates a region where wraparound cannot be performed because there is an organ, and a mark "○" indicates a region where wraparound can be performed. When the user visually recognizes the path selection image C3 and designates a number by voice, a wraparound path corresponding to the position of the number is selected, and the camerawork is determined on the basis of the selected wraparound path. An operative field image is generated by the image processing unit 1061 according to the camerawork.

For example, the user visually recognizes the display image, emits "2", and selects a desired wraparound path. The voice is detected by the voice detection unit 2202 and recognized by the voice recognition unit 2020. Imaging is executed on the basis of the wraparound path of "2", an operative field image is generated by the image processing unit 1061 according to the imaging, and the generated operative field image is displayed by the display device 1041. Note that the path selection image C3 is no longer displayed at a predetermined timing after the number is selected. The predetermined timing may be a timing after a predetermined time from the completion of the number selection, or may be a timing instructed by an input operation by the user.

According to such a seventh processing example, in a case where the user feels that the wraparound path selection is necessary, it is possible to easily select the wraparound path using the path selection image C3 functioning as the path selection GUI. As a result, the provision of the operative field image desired by the user can be continued.

1-2-8. GUI Variations

GUIs according to the present embodiment, that is, variations of the position adjustment image will be described with reference to FIGS. 10 to 13. FIGS. 10 to 13 are diagrams for explaining variations of the position adjustment image according to the present embodiment.

Figure 10:
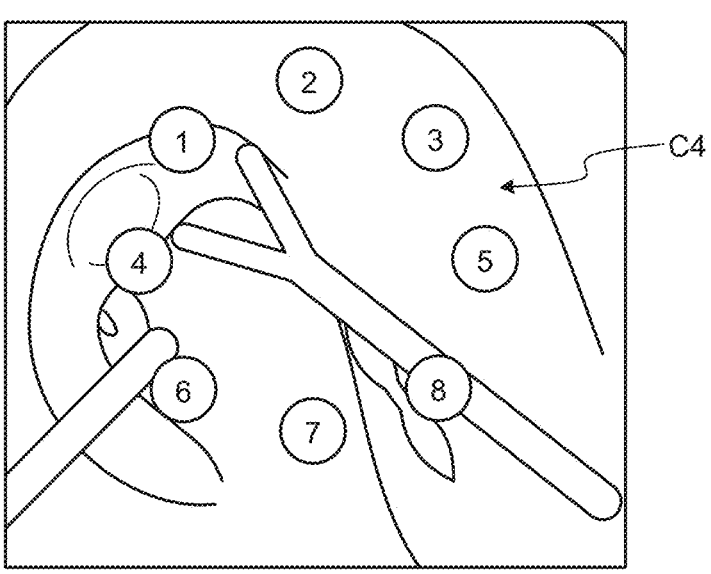
FIG. 10 is a diagram for explaining variations of the position adjustment image according to an embodiment of the present disclosure.

As illustrated in FIG. 10, similarly to FIG. 7, the position adjustment image C4 is an image for the user to adjust the position of the tracking target in the XY directions. In the example of FIG. 10, the position adjustment image C4 is an image for the user to designate a position for centering the tracking target in the operative field image. In the position adjustment image C4, a plurality of numbers (for example, 1 to 8) is arranged in a circular shape. When the user designates a number by voice, the operative field image is adjusted by the image processing unit 1061 such that the position of the number becomes the center of the operative field image.

Figure 11:
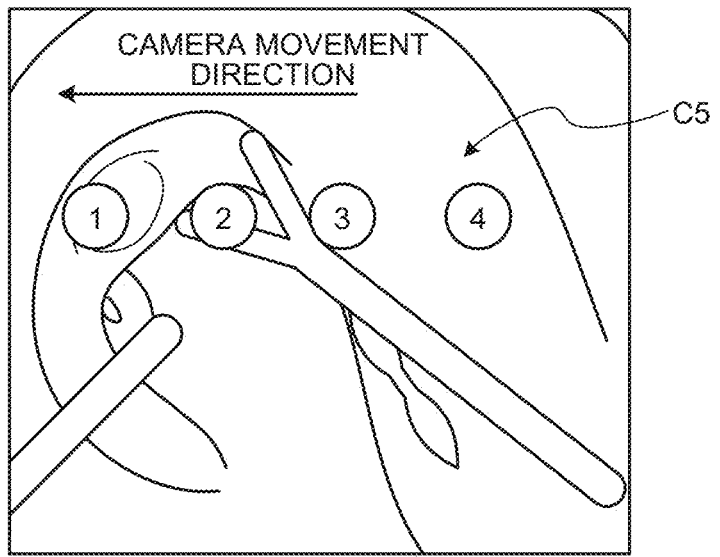
FIG. 11 is a diagram for explaining variations of the position adjustment image according to an embodiment of the present disclosure.

As illustrated in FIG. 11, the position adjustment image C5 is an image for the user to adjust the position of the tracking target in the X direction. In the example of FIG. 11, the position adjustment image C5 is an image for the user to designate a position for centering the tracking target in the X direction of the operative field image. In the position adjustment image C5, a plurality of numbers (for example, 1 to 4) is linearly arranged. When the user designates a number by voice, the operative field image is adjusted by the image processing unit 1061 such that the position of the number is at the center of the operative field image in the X direction.

Figure 12:
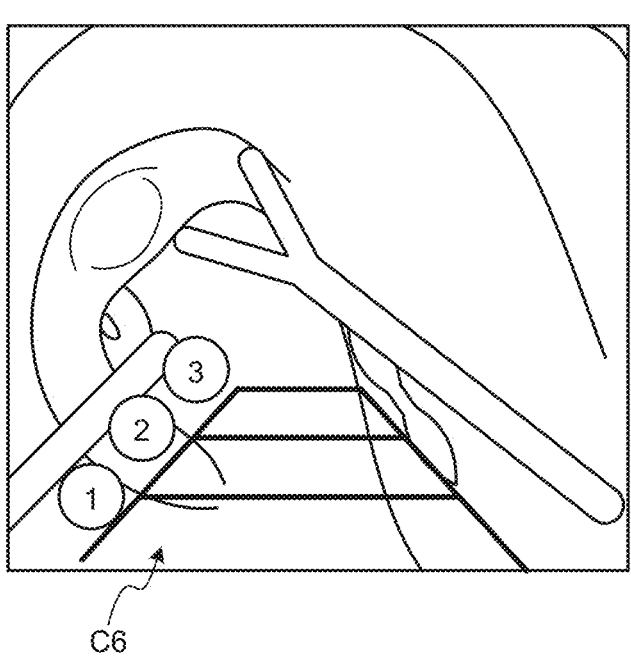
FIG. 12 is a diagram for explaining variations of the position adjustment image according to an embodiment of the present disclosure.

As illustrated in FIG. 12, the position adjustment image C6 is an image for the user to adjust the position of the tracking target in the Z direction, similarly to FIG. 8. In the example of FIG. 12, the position adjustment image C5 is an image for the user to designate the position of the tracking target in the Z direction, that is, the position in the depth direction. In the position adjustment image C6, trapezoidal graduations representing the depth are arranged, and the numerical value of the graduations is, for example, 1 to 3. When the user designates a number by voice, zooming is performed to a position in the depth direction corresponding to the position of the number, and the operative field image is adjusted by the image processing unit 1061.

Figure 13:
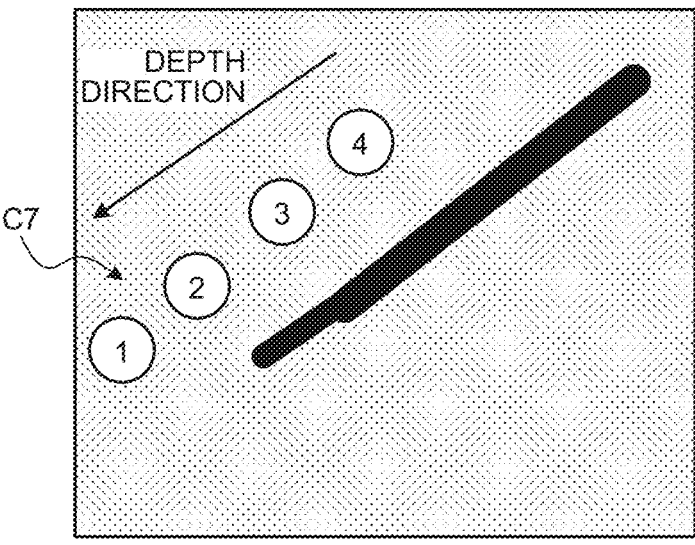
FIG. 13 is a diagram for explaining variations of the position adjustment image according to an embodiment of the present disclosure.

As illustrated in FIG. 13, the position adjustment image C7 is an image for the user to adjust the position of the tracking target in the Z direction, similarly to FIG. 8. In the example of FIG. 13, the position adjustment image C5 is an image for the user to designate the position of the tracking target in the Z direction, that is, the position in the depth direction. In the position adjustment image C7, a plurality of numbers (for example, 1 to 4) is arranged along the depth direction. When the user designates a number by voice, zooming is performed to a position in the depth direction corresponding to the position of the number, and the operative field image is adjusted by the image processing unit 1061.

1-3. Example of Tracking Processing of Endoscopic Surgery System

1-3-1. Overall Process Flow

Figure 14:
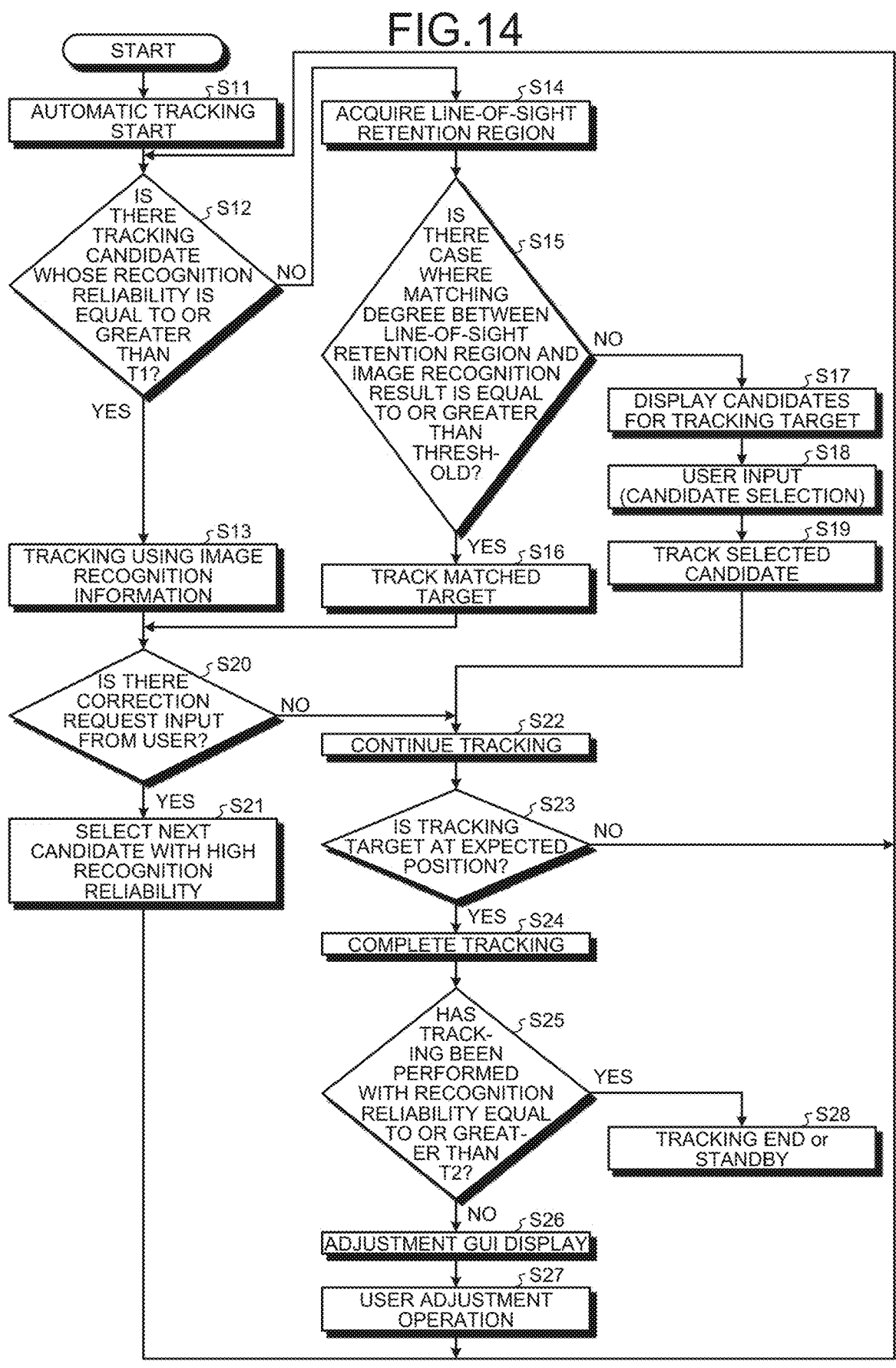
FIG. 14 is a flowchart illustrating a flow of an example of tracking processing of the endoscopic surgery system according to an embodiment of the present disclosure.

An example of tracking processing of the endoscopic surgery system 1000 according to the present embodiment will be described with reference to FIG. 14. FIG. 14 is a flowchart illustrating a flow of an example of tracking processing of the endoscopic surgery system 1000 according to the present embodiment.

As illustrated in FIG. 14, in Step S11, the automatic tracking processing is started by the endoscopic surgery system 1000. In Step S12, the target determination unit 2003 determines whether or not there is a tracking candidate (tracking target candidate) whose recognition reliability is equal to or greater than a predetermined threshold T1. When it is determined in Step S12 that there is a tracking candidate whose recognition reliability is equal to or greater than the predetermined threshold T1 (Yes in Step S12), the tracking candidate is determined as a tracking target and tracking control using image recognition information is executed in Step S13. On the other hand, when it is determined that there is no tracking candidate having the recognition reliability equal to or greater than the predetermined threshold T1 (No in Step S12), the line-of-sight retention region (for example, the line-of-sight retention area G1) is acquired by the line-of-sight information processing unit 2010 in Step S14. Note that the predetermined threshold T1 is an index of whether or not to start tracking based on the image recognition information.

In Step S15, the target determination unit 2003 determines whether or not there is a case where a matching degree between the line-of-sight retention region and the image recognition result is equal to or greater than the predetermined threshold. When it is determined in Step S15 that there is a case where the matching degree between the line-of-sight retention region and the image recognition result is equal to or greater than the predetermined threshold (Yes in Step S15), in Step S16, the target having the matching degree equal to or greater than the predetermined threshold, that is, the matched target is set as the tracking target by the target determination unit 2003 (see, for example, FIG. 3). On the other hand, when it is determined in Step S15 that there is no case where the matching degree between the line-of-sight retention region and the image recognition result is equal to or greater than the predetermined threshold (No in Step S15), candidates for the tracking target are displayed in Step S17. In Step S18, a candidate is selected by a user input. In Step S19, the selected candidate is set as a tracking target (see, for example, FIGS. 4 and 5).

In Step S20, the target determination unit 2003 determines whether or not there is a correction request input from the user. When it is determined in Step S20 that there is a correction request input from the user (Yes in Step S20), a next candidate with high recognition reliability is selected by the target determination unit 2003 in Step S21, and the process returns to Step S12. On the other hand, when it is determined in Step S20 that there is no correction request input from the user (No in Step S20), tracking is continued in Step S22.

In Step S23, the control unit 1063 determines whether or not the tracking target is at the expected position. When it is determined in Step S23 that the tracking target is not positioned at the expected position (No in Step S23), the process returns to Step S12. On the other hand, when it is determined in Step S23 that the tracking target is at the expected position (Yes in Step S23), the tracking is completed in Step S24.

In Step S25, the control unit 1063 determines whether or not tracking has been performed with the recognition reliability equal to or greater than a predetermined threshold T2. When it is determined in Step S25 that tracking is not performed with the recognition reliability being equal to or greater than the predetermined threshold T2 (No in Step S25), an adjustment GUI (for example, the position adjustment images C1, C2, and C4 to C7) is displayed on the display device 1041 in Step S26 (see, for example, FIGS. 7, 8, and 10 to 13). In Step S27, the user adjustment operation is executed, and the process returns to Step S12. On the other hand, when it is determined in Step S25 that the tracking has been performed with the recognition reliability equal to or greater than the predetermined threshold T2 (Yes in Step S25), the tracking end or the tracking standby is executed. Note that the predetermined threshold T2 is an index indicating whether or not to display the adjustment GUI.

1-3-2. Flow During Main Steps in Entire Process

Figure 15:
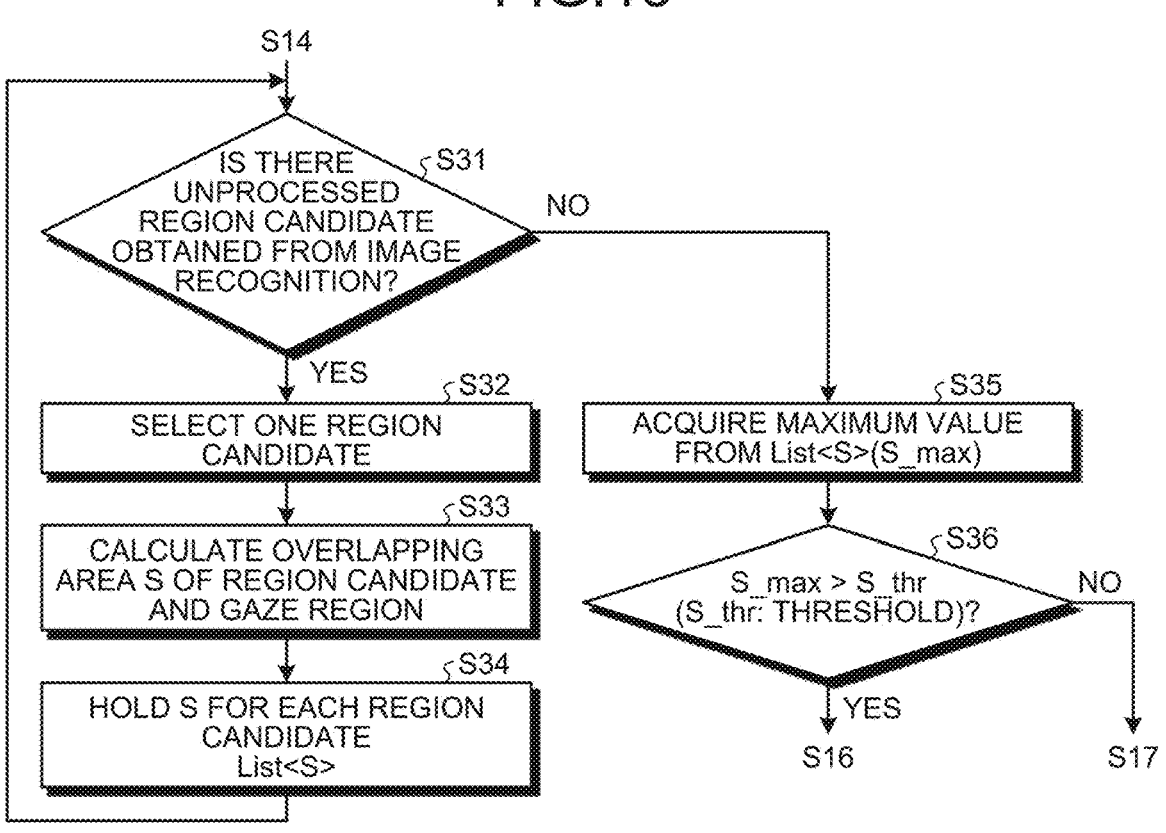
FIG. 15 is a flowchart illustrating a flow during some steps in FIG. 14.
Figure 16:
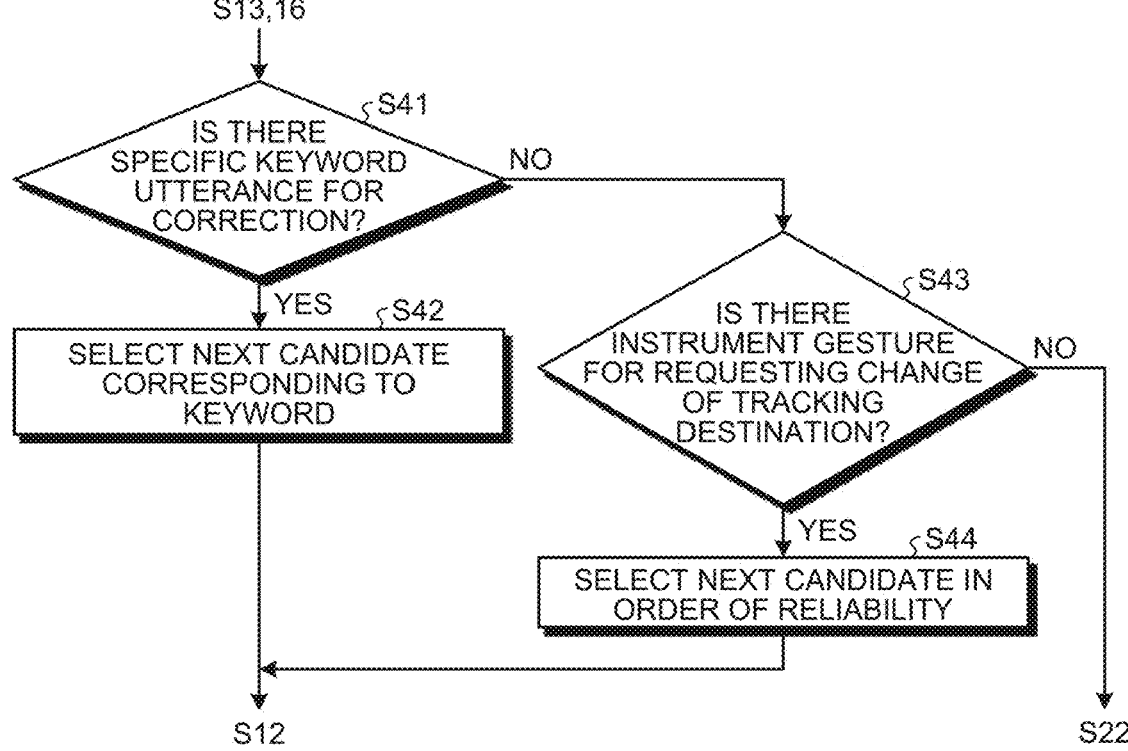
FIG. 16 is a flowchart illustrating a flow during some steps in FIG. 14.
Figure 17:
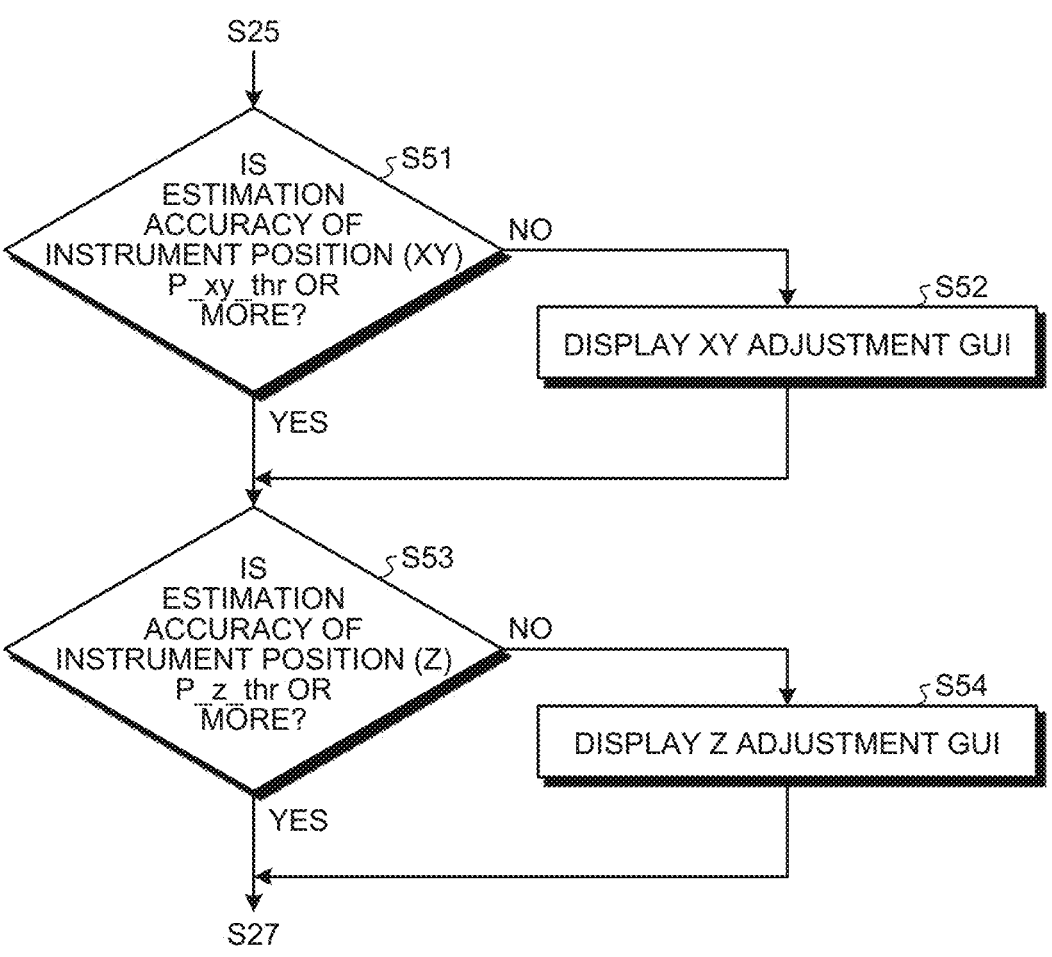
FIG. 17 is a flowchart illustrating a flow during some steps in FIG. 14.

Next, main Steps S15, S20, S21, and S26 in FIG. 14 will be described with reference to FIGS. 15 to 17. FIGS. 15 to 17 are flowcharts each illustrating a flow during some steps in FIG. 14.
(Step S15)

As illustrated in FIG. 15, in Step S31, the target candidate recognition unit 2001 determines whether or not there is an unprocessed region candidate (tracking target candidate) obtained from image recognition. When it is determined in Step S31 that there is an unprocessed region (Yes in Step S31), one region candidate is selected from a plurality of region candidates in Step S32. In Step S33, the target candidate recognition unit 2001 calculates an overlapping area S of the region candidate and the gaze region (for example, the line-of-sight retention area G1). In Step S34, the overlapping area S is held for each region candidate, a list (List <S>) of the overlapping areas S is generated, and the process returns to Step S31.

Here, the list of the overlapping areas S is stored by the target candidate recognition unit 2001, for example. The target candidate recognition unit 2001 includes a storage unit that stores various types of information such as a list of the overlapping areas S. The storage unit is implemented by, for example, a semiconductor memory element such as a random access memory (RAN) or a flash memory, or a storage device such as a hard disk or an optical disk.

When it is determined in Step S31 that there is no unprocessed region (No in Step S31), the maximum value S_max is acquired from the list of the overlapping areas S (List <S>) by the target candidate recognition unit 2001 in Step S35. In Step S36, the target candidate recognition unit 2001 determines whether or not the maximum value S_max is larger than a predetermined threshold S_thr. When it is determined that the maximum value S_max is larger than the predetermined threshold S_thr (Yes in Step S36), the region candidate having the maximum value S_max is targeted, and the process proceeds to Step S16. On the other hand, when it is determined that the maximum value S_max is not larger than the predetermined threshold S_thr (No in Step S36), the process proceeds to Step S17.
(Steps S20 and S21)

As illustrated in FIG. 16, in Step S41, the target candidate recognition unit 2001 determines whether or not there is a specific keyword utterance for correction. When it is determined in Step S41 that there is the specific keyword utterance for correction (Yes in Step S41), the next candidate corresponding to the keyword is selected by the target candidate recognition unit 2001 in Step S42, and the process proceeds to Step S12.

On the other hand, when it is determined in Step S41 that there is no specific keyword utterance for correction (No in Step S41), in Step S43, the target candidate recognition unit 2001 determines whether or not there is an instrument gesture for requesting the change of the tracking destination. When it is determined in Step S43 that there is an instrument gesture (Yes in Step S43), the next candidate in the order of recognition reliability is selected by the target candidate recognition unit 2001, and the process proceeds to Step S12. On the other hand, when it is determined in Step S43 that there is no instrument gesture (No in Step S43), the process proceeds to Step S22.

(Step S26)

As illustrated in FIG. 17, in Step S51, the target determination unit 2003 determines whether or not the estimation accuracy of the instrument position (XY) is a predetermined threshold P_xy_thr or more. When it is determined in Step S51 that the estimation accuracy of the instrument position (XY) is not the predetermined threshold P_xy_thr or more (No in Step S51), an XY adjustment GUI (for example, the position adjustment images C1, C4, and C5) is generated by the image processing unit 1061 and displayed on the display device 1041 in Step S52. Thereafter, the process proceeds to Step S53. On the other hand, when it is determined in Step S51 that the estimation accuracy of the instrument position (XY) is the predetermined threshold P_xy_thr or more (Yes in Step S51), the process proceeds to Step S53.

In Step S53, the target determination unit 2003 determines whether or not the estimation accuracy of the instrument position (Z) is a predetermined threshold P_z_thr or more. When it is determined in Step S53 that the estimation accuracy of the instrument position (Z) is not the predetermined threshold P_z_thr or more (No in Step S53), a Z adjustment GUI (for example, the position adjustment images C2, C6, and C7) is generated by the image processing unit 1061 and displayed on the display device 1041 in Step S54. Thereafter, the process proceeds to Step S27. On the other hand, when it is determined in Step S53 that the estimation accuracy of the instrument position (Z) is the predetermined threshold P_z_thr or more (Yes in Step S53), the process proceeds to Step S27.

Figure 18:
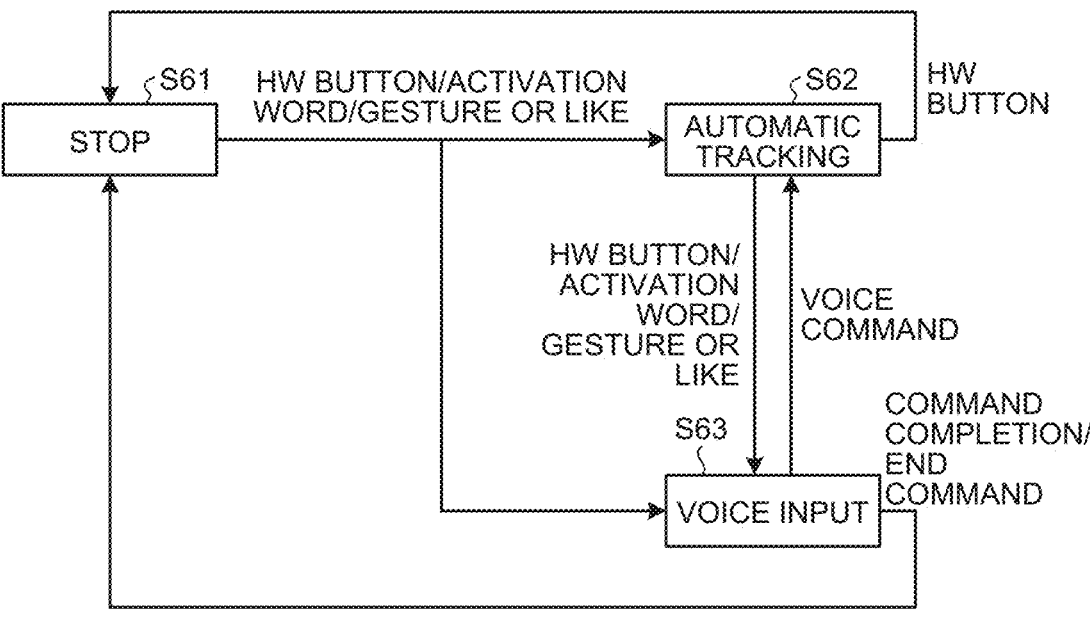
FIG. 18 is a diagram for explaining an example of trigger operation of start and stop of automatic tracking and voice input according to an embodiment of the present disclosure.

1-4. Example of Trigger Operation for Start and Stop of Automatic Tracking and Voice Input An example of trigger operation of start and stop of automatic tracking and voice input according to the present embodiment will be described with reference to FIG. 18. FIG. 18 is a diagram for explaining an example of trigger operation of start and stop of automatic tracking and voice input according to the present embodiment.

As illustrated in FIG. 18, when pressing of the HW button (hardware button), an activation word, a gesture, or the like is detected as a start trigger in the automatic tracking stop state in Step S61, the automatic tracking stop state in Step S61 shifts to the automatic tracking state (automatic tracking start) in Step S62 and the voice input state in Step S63 (voice input start). The voice input state in Step S63 is a voice command input waiting state.

When the pressing of the HW button is detected as a stop trigger in the automatic tracking state in Step S62, the automatic tracking state in Step S62 shifts to the automatic tracking stop state in Step S61 (automatic tracking stop). In addition, when a command completion/end command by voice input is detected as a stop trigger in the voice input state in Step S63, the voice input state in Step S63 shifts to the automatic tracking stop state in Step S61 (voice input stop).

Note that, when pressing of the HW button, an activation word, a gesture, or the like is detected as a voice input trigger in the automatic tracking state in Step S62, and a voice command by voice input is detected in the voice input state in Step S63, the voice command is sent to the automatic tracking state in Step S62. At this time, the control is executed according to the voice command.

In this manner, the automatic tracking stop state, the automatic tracking state, and the voice input state are switched by the control unit 1063, for example, and trigger operations of start and stop of automatic tracking and voice input are implemented. That is, the start and stop of the automatic tracking, the voice input, and the like are switched in response to the pressing of the HW button, the detection of the activation word, the gesture, or the like, but the present invention is not limited thereto. Furthermore, the pressing of the HW button, the activation word, the gesture, or the like is basically performed by the user such as the operator 1067, but is not limited thereto, and may be performed by a user such as an assistant, for example. Furthermore, the gesture may be an operation of the user himself/herself such as the operator 1067 or an assistant, or may be an operation of an instrument or the like operated by the user (for example, an opening/closing operation, a swing operation, or the like).

1-5. Actions and Effects

As described above, the endoscopic surgery system 1000 according to the present embodiment includes: an imaging unit 1009 that acquires an operative field image including an abdominal cavity environment; a display unit (for example, display device 1041) that displays the operative field image acquired by the imaging unit 1009; a gaze information acquisition unit (for example, line-of-sight information processing unit 2010) that acquires information regarding gaze of a user on the abdominal cavity environment of the operative field image displayed by the display unit; a target candidate recognition unit 2001 that recognizes a tracking target candidate from the operative field image acquired by the imaging unit 1009; a reliability acquisition unit 2002 that acquires recognition reliability of the tracking target candidate recognized by the target candidate recognition unit 2001; and a target determination unit 2003 that determines a tracking target in the abdominal cavity environment from the tracking target candidate on the basis of the information regarding the tracking target candidate recognized by the target candidate recognition unit 2001, the recognition reliability acquired by the reliability acquisition unit 2002, and the information regarding the gaze acquired by the gaze information acquisition unit. As a result, it is possible to determine the tracking target in the operative field image on the basis of the recognition reliability and the information regarding the gaze in addition to the information regarding the tracking target candidate. Therefore, even in a situation where image recognition cannot be performed well, the automatic tracking accuracy with respect to the tracking target can be improved.

Furthermore, the target determination unit 2003 may determine the tracking target from the tracking target candidates according to a predetermined threshold of the preset recognition reliability. As a result, it is possible to improve the automatic tracking accuracy with respect to the tracking target by adjusting the predetermined threshold of the recognition reliability.

Furthermore, in a case where the recognition reliability acquired by the reliability acquisition unit 2002 is less than the predetermined threshold, the target determination unit 2003 may use information regarding gaze. As a result, when the recognition reliability is less than the predetermined threshold, processing based on the information regarding gaze can be executed, and the automatic tracking accuracy for the tracking target can be improved.

Furthermore, the information regarding the tracking target candidate includes information regarding a recognition region of the tracking target candidate, the information regarding the gaze includes information regarding a gaze region (for example, line-of-sight retention area G1) of the user, and the target determination unit 2003 may determine the tracking target candidate according to an overlapping area between the recognition region of the tracking target candidate and the gaze region of the user. As a result, the tracking target can be accurately determined on the basis of the information regarding the recognition region of the tracking target candidate and the information regarding the gaze region of the user.

Furthermore, the target determination unit 2003 may calculate an overlapping area between the recognition region of the tracking target candidate and the gaze region of the user for each tracking target candidate, and determine the tracking target candidate having the largest overlapping area as the tracking target. As a result, the tracking target can be more accurately determined on the basis of the information regarding the recognition region of the tracking target candidate and the information regarding the gaze region.

Furthermore, the endoscopic surgery system 1000 may further include an input unit (for example, input device 1047) that receives information regarding the voice of the user and the operation of the tracking target candidate. As a result, it is possible to perform processing based on the information regarding the voice of the user and the operation of the tracking target candidate.

Furthermore, the target determination unit 2003 may determine the tracking target on the basis of at least one of the information regarding the voice of the user or the information regarding the operation of the tracking target candidate. As a result, it is possible to determine the tracking target in the abdominal cavity environment on the basis of at least one of the information regarding the voice of the user or the information regarding the operation of the tracking target candidate, and thus, it is possible to improve the automatic tracking accuracy with respect to the tracking target.

Furthermore, the information regarding the voice of the user is a correction request, and the target determination unit 2003 may determine a tracking target candidate having higher recognition reliability as the tracking target in response to the correction request. As a result, a tracking target candidate with higher recognition reliability can be determined as a tracking target in response to the correction request of the user, so that the automatic tracking accuracy for the tracking target can be improved.

Furthermore, the target determination unit 2003 may determine continuation and stop of the processing of determining the tracking target according to whether or not the tracking target is at a predetermined expected position. As a result, in a case where the tracking target is at the predetermined expected position, it is possible to stop the processing of determining the tracking target, and thus, it is possible to suppress the execution of unnecessary processing.

Furthermore, the target determination unit 2003 may determine the tracking target on the basis of the information regarding the gaze in a case where the information regarding the tracking target candidate cannot be acquired. As a result, even in a case where the recognition information cannot be acquired, that is, in a case where a loss occurs in which the tracking target is lost, the tracking target can be determined on the basis of the line-of-sight information, so that the tracking operation can be continued.

Furthermore, the target candidate recognition unit 2001 may recognize a tracking target candidate on the basis of information regarding gaze. This makes it possible to acquire tracking target candidates even in a situation where image recognition cannot be performed well, and thus, it is possible to further improve the automatic tracking accuracy with respect to the tracking target.

Furthermore, the recognition reliability may be a probability indicating whether or not the tracking target candidate is within a predetermined target region (for example, a bounding box). As a result, the tracking target can be determined on the basis of the probability indicating whether or not the tracking target candidate is accurately within the predetermined target region.

Furthermore, the recognition reliability may include the recognition reliability with respect to the position in the planar direction or the depth direction of the tracking target candidate. As a result, the tracking target can be determined on the basis of the recognition reliability with respect to the position in the planar direction or the depth direction of the tracking target candidate.

Furthermore, the recognition reliability may include the recognition reliability for the type of the tracking target candidate. As a result, the tracking target can be determined on the basis of the recognition reliability for the type of the tracking target candidate.

Furthermore, the display unit may display information for identifying a plurality of tracking target candidates in superposition with the operative field image. As a result, the user can identify and select each tracking target candidate.

Furthermore, the display unit may display a position adjustment image (for example, position adjustment images C1, C2, and C4 to C7) for adjusting the position in the planar direction or the depth direction of the tracking target determined by the target determination unit 2003, in superposition with the operative field image. As a result, the user can adjust the position of the tracking target in the planar direction or the depth direction.

Furthermore, the display unit may display the position adjustment image according to the recognition reliability of the tracking target candidate recognized by the target candidate recognition unit 2001. As a result, the position adjustment image can be displayed according to the recognition reliability.

Furthermore, the endoscopic surgery system 1000 may further include an input unit (for example, input device 1047) that receives information regarding a voice of the user or an input operation of the user, and a control unit 1063 that switches an automatic tracking state of tracking the tracking target, a voice input state of receiving the voice of the user, and an automatic tracking stop state in which tracking of the tracking target is stopped according to the information regarding the voice of the user or the input operation of the user according to the information regarding the voice and the input operation of the user. As a result, the user can control the automatic tracking state, the voice input state, and the automatic tracking stop state.

Furthermore, the endoscopic surgery system 1000 may further include an arm portion 1031 that supports and moves the imaging unit 1009, and an arm control unit (for example, arm control device 1045) that controls the arm portion 1031 so that the tracking target determined by the target determination unit 2003 is positioned in the operative field image. As a result, the tracking operation by the arm portion 1031 can be performed.

Furthermore, the endoscopic surgery system 1000 may further include an input unit (for example, input device 1047) that receives information regarding an operation of the arm portion 1031, and the arm control unit may control the arm portion 1031 on the basis of the information regarding the operation of the arm portion 1031. As a result, it is possible to reduce the burden on the doctor and improve the accuracy of the arm control by a combination of the autonomous control and the manual control.

Furthermore, the endoscopic surgery system 1000 may further include an image processing unit 1061 that generates an operative field image such that the tracking target determined by the target determination unit 2003 is positioned in the operative field image. As a result, a tracking operation by image processing can be performed.

2. OTHER EMBODIMENTS

The processing according to the above-described embodiments (or modifications) may be performed in various different modes (modifications) other than the above-described embodiments. For example, among the processes described in the above embodiments, all or a part of the processes described as being automatically performed can be manually performed, or all or a part of the processes described as being manually performed can be automatically performed by a known method. In addition, the processing procedure, specific name, and information including various data and parameters illustrated in the document and the drawings can be arbitrarily changed unless otherwise specified. For example, the various types of information illustrated in each figure are not limited to the illustrated information.

In addition, each component of each device illustrated in the drawings is functionally conceptual, and is not necessarily physically configured as illustrated in the drawings. That is, a specific form of distribution and integration of each device is not limited to the illustrated form, and all or a part thereof can be functionally or physically distributed and integrated in an arbitrary unit according to various loads, usage conditions, and the like.

In addition, the above-described embodiments (or modifications) can be appropriately combined within a range that does not contradict processing contents. Furthermore, the effects described in the present specification are merely examples and are not limited, and other effects may be provided.

In addition, in the above-described embodiments (or modifications), a system means a set of a plurality of components (devices, modules (parts), and the like), and it does not matter whether or not all the components are in the same housing. Therefore, a plurality of devices housed in separate housings and connected via a network and one device in which a plurality of modules is housed in one housing are both systems.

Furthermore, in the above-described embodiments (or modifications), a configuration of cloud computing in which one function is shared and processed in cooperation by a plurality of devices via a network can be adopted. Furthermore, each step described in the above-described processing flow (for example, a flowchart) can be executed by one device or can be shared and executed by a plurality of devices. Furthermore, in a case where a plurality of processes is included in one step, the plurality of processes included in the one step can be executed by one device or can be shared and executed by a plurality of devices.

3. APPLICATION EXAMPLE

The technology according to the present disclosure can be applied to a medical imaging system. The medical imaging system is a medical system using an imaging technology, and is, for example, the above-described endoscope system or microscope system. That is, the technology according to the present disclosure may be applied to a microscope system.

Figure 19:
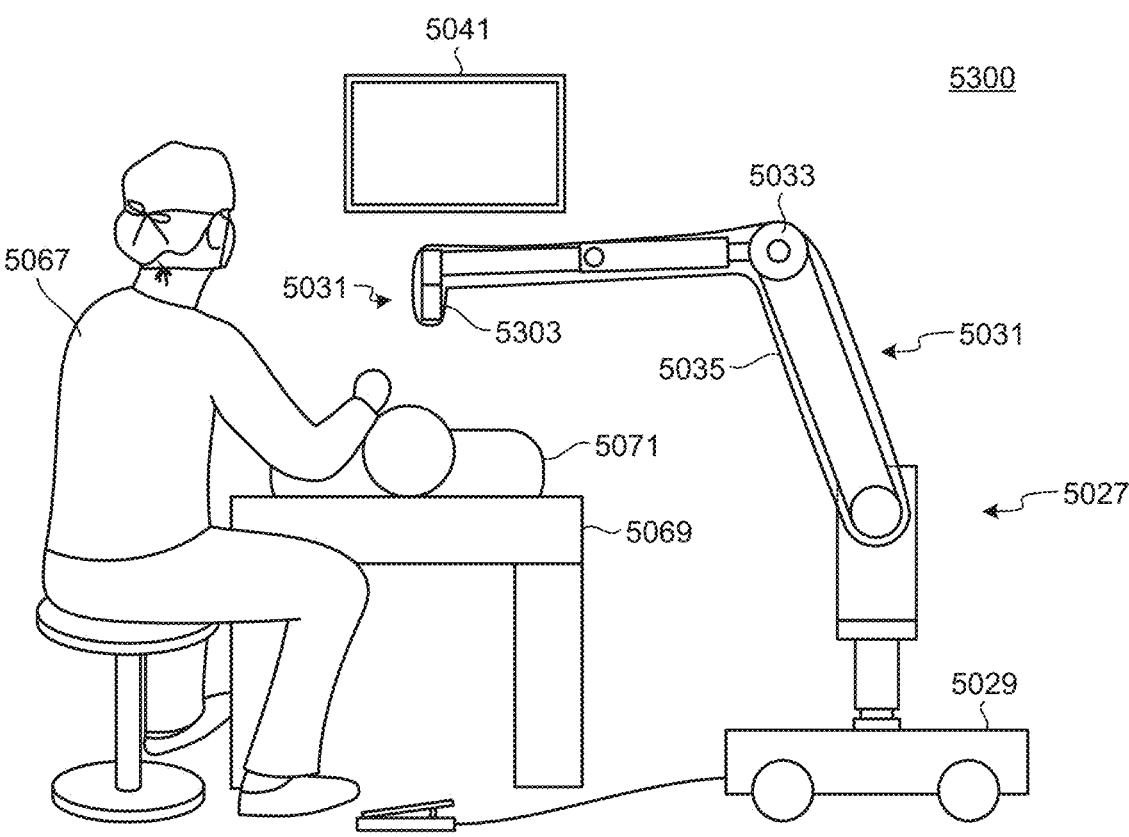
FIG. 19 is a diagram illustrating an example of a schematic configuration of a microscopic surgery system.

FIG. 19 is a diagram illustrating an example of a schematic configuration of a microscopic surgery system 5300 to which the technology according to the present disclosure is applicable. In the following description, the same components as those of the endoscopic surgery system 1000 will be denoted by the same reference numerals, and the description thereof will not be repeated.

FIG. 19 schematically illustrates a situation where an operator 5067 performs an operation on a patient 5071 on a patient bed 5069 using a microscopic surgery system 5300. For the sake of simplicity, FIG. 19 does not illustrate the cart 1037 among the components of the microscopic surgery system 5300, and illustrates a microscope device 5301 instead of the endoscope 1001 in a simplified manner. The microscope device 5301 may refer to a microscope 5303 provided at the distal end of the links 5035, or may refer to the overall configuration including the microscope 5303 and a support device 5027.

As illustrated in FIG. 19, during the operation, the microscopic surgery system 5300 is used to display an image of a surgical site captured by the microscope device 5301 in a magnified manner on a display device 5041 installed in the operating room. The display device 5041 is installed in a position facing the operator 5067, and the operator 5067 performs various procedures, such as excision of an affected part, on the surgical site while observing the state of the surgical site using the image displayed on the display device 5041. The microscopic surgery system 5300 is used in, for example, ophthalmic operation and neurosurgical operation.

The example of the microscopic surgery system 5300 to which the technology according to the present disclosure is applicable has been described above. Systems to which the technology according to the present disclosure is applicable are not limited to such examples. For example, the support device 5027 can support, at the distal end thereof, another observation device or another surgical tool instead of the endoscope 1001 or the microscope 5303. Examples of the other applicable observation devices and other surgical tools include forceps, tweezers, a pneumoperitoneum tube for pneumoperitoneum, and an energy treatment tool for incising a tissue or sealing a blood vessel by cauterization. By using the support device to support the observation device or the surgical tool described above, the position thereof can be more stably fixed and the load of the medical staff can be lower than in a case where the medical staff manually supports the observation device or the surgical tool. The technology according to the present disclosure may be applied to a support device for supporting such a component other than the microscope 5303.

The technology according to the present disclosure can be suitably applied to medical observation systems such as the endoscopic surgery system 1000 and the microscopic surgery system 5300. By applying the technology according to the present disclosure to the medical observation system, it is possible to determine the tracking target in the operative field image on the basis of the line-of-sight information in addition to the recognition information, and thus, it is possible to improve the automatic tracking accuracy with respect to the tracking target.

4. CONFIGURATION EXAMPLE OF HARDWARE

Figure 20:
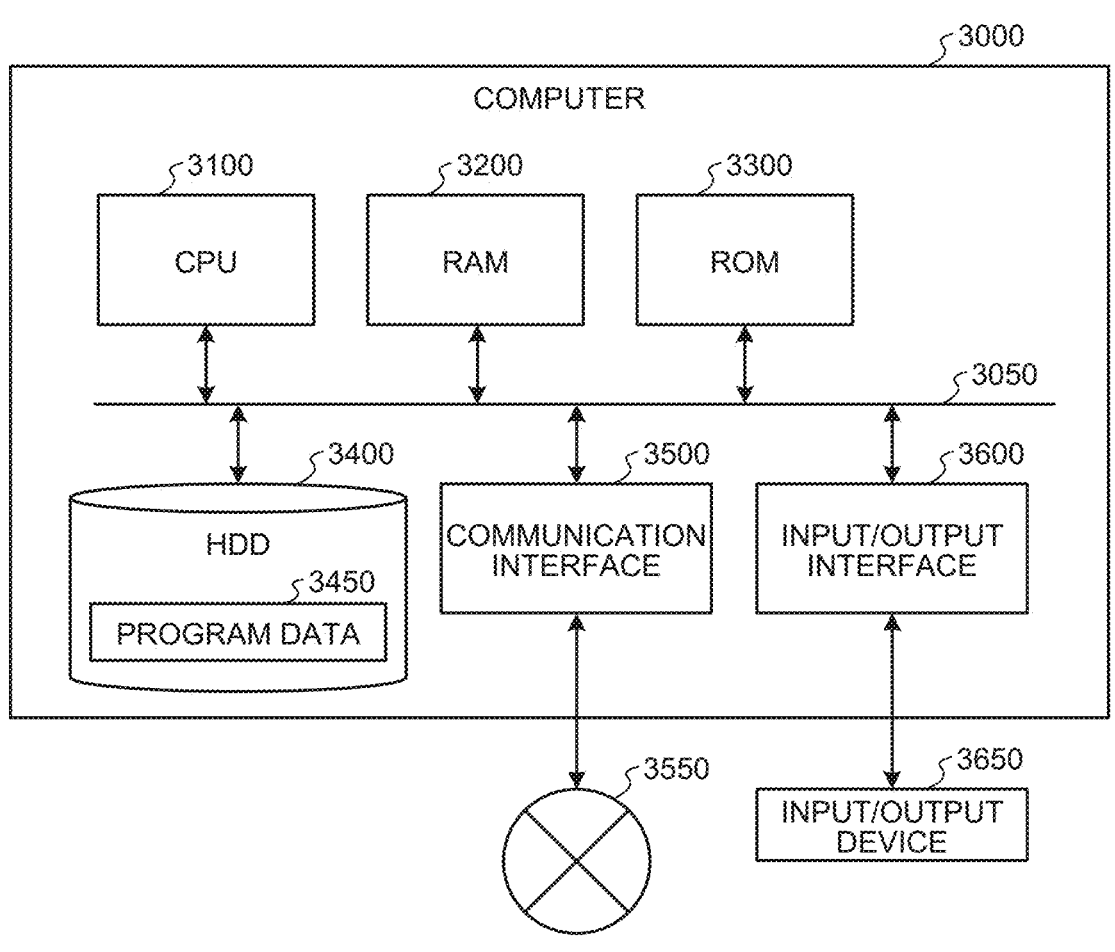
FIG. 20 is a diagram illustrating an example of a schematic configuration of hardware.

The information processing apparatus such as the CCU 1039 described above is implemented by, for example, a computer 3000 having a configuration as illustrated in FIG. 20. FIG. 20 is a diagram illustrating a schematic configuration of hardware of the computer 3000.

As illustrated in FIG. 20, the computer 3000 includes a CPU 3100, a RAM 3200, a read only memory (ROM) 3300, a hard disk drive (HDD) 3400, a communication interface 3500, and an input/output interface 3600. Each unit of the computer 3000 is connected by a bus 3050.

The CPU 3100 operates on the basis of a program stored in the ROM 3300 or the HDD 3400, and controls each unit. For example, the CPU 3100 develops a program stored in the ROM 3300 or the HDD 3400 in the RAM 3200, and executes processing corresponding to various programs.

The ROM 3300 stores a boot program such as a basic input output system (BIOS) executed by the CPU 3100 when the computer 3000 is activated, a program depending on hardware of the computer 3000, and the like.

The HDD 3400 is a computer-readable recording medium that non-transiently records a program executed by the CPU 3100, data used by the program, and the like. Specifically, the HDD 3400 is a recording medium that records an information processing program according to the present disclosure as an example of program data 3450.

The communication interface 3500 is an interface for the computer 3000 to connect to an external network 3550 (for example, the Internet). For example, the CPU 3100 receives data from another device or transmits data generated by the CPU 3100 to another device via the communication interface 3500.

The input/output interface 3600 is an interface for connecting an input/output device 3650 and the computer 3000. For example, the CPU 3100 receives data from an input device such as a keyboard and a mouse via the input/output interface 3600. In addition, the CPU 3100 transmits data to an output device such as a display, a speaker, or a printer via the input/output interface 3600. Furthermore, the input/output interface 3600 may function as a media interface that reads a program or the like recorded in a predetermined recording medium (medium). The medium is, for example, an optical recording medium such as a digital versatile disc (DVD) or a phase change rewritable disk (PD), a magneto-optical recording medium such as a magneto-optical disk (MO), a tape medium, a magnetic recording medium, a semiconductor memory, or the like.

For example, in a case where the computer 3000 functions as the CCU 1039, the CPU 3100 of the computer 3000 implements the functions of the respective units of the CCU 1039 by executing the information processing program loaded on the RAM 3200. In addition, the HDD 3400 stores an information processing program and various data. Note that the CPU 3100 reads the program data 3450 from the HDD 3400 and executes the program data, but as another example, these programs may be acquired from another device via the external network 3550.

5. APPENDIX

Note that the present technology can also have the following configurations.

(1)

A medical observation system comprising:

an imaging unit that acquires an operative field image including an abdominal cavity environment;

a display unit that displays the operative field image acquired by the imaging unit;

a gaze information acquisition unit that acquires information regarding gaze of a user on the abdominal cavity environment of the operative field image displayed by the display unit;

a target candidate recognition unit that recognizes a tracking target candidate from the operative field image acquired by the imaging unit;

a reliability acquisition unit that acquires recognition reliability of the tracking target candidate recognized by the target candidate recognition unit; and a target determination unit that determines a tracking target in the abdominal cavity environment from the tracking target candidate on a basis of the information regarding the tracking target candidate recognized by the target candidate recognition unit, the recognition reliability acquired by the reliability acquisition unit, and the information regarding the gaze acquired by the gaze information acquisition unit.

(2)

The medical observation system according to (1), wherein the target determination unit determines the tracking target from the tracking target candidate according to a predetermined threshold of the recognition reliability preset.

(3)

The medical observation system according to (2), wherein the target determination unit uses the information regarding the gaze in a case where the recognition reliability acquired by the reliability acquisition unit is less than the predetermined threshold.

(4)

The medical observation system according to any one of (1) to (3), wherein the information regarding the tracking target candidate includes information regarding a recognition region of the tracking target candidate, the information regarding the gaze includes information regarding a gaze region of the user, and the target determination unit determines the tracking target according to an overlapping area of the recognition region and the gaze region.

(5)

The medical observation system according to (4), wherein the target determination unit calculates an overlapping area between the recognition region and the gaze region for each of the tracking target candidate, and determines the tracking target candidate having the overlapping area being largest as the tracking target.

(6)

The medical observation system according to any one of (1) to (5), further comprising an input unit that receives information regarding a voice of the user and an operation of the tracking target candidate.

(7)

The medical observation system according to (6), wherein the target determination unit determines the tracking target on a basis of at least one of the information regarding the voice of the user or the information regarding the operation of the tracking target candidate.

(8)

The medical observation system according to (7), wherein the information regarding the voice of the user is a correction request, and the target determination unit determines the tracking target candidate having the recognition reliability being higher as the tracking target in response to the correction request.

(9)

The medical observation system according to any one of (1) to (8), wherein the target determination unit determines continuation and stop of processing of determining the tracking target according to whether or not the tracking target is at a predetermined expected position.

(10)

The medical observation system according to any one of (1) to (9), wherein the target determination unit determines the tracking target on a basis of the information regarding the gaze in a case where the target determination unit cannot acquire the information regarding the tracking target candidate.

(11)

The medical observation system according to any one of (1) to (10), wherein the target candidate recognition unit recognizes the tracking target candidate on a basis of the information regarding the gaze.

(12)

The medical observation system according to any one of (1) to (11), wherein the recognition reliability is a probability indicating whether or not the tracking target candidate is within a predetermined target region.

(13)

The medical observation system according to any one of (1) to (12), wherein the recognition reliability includes recognition reliability with respect to a position in a planar direction or a depth direction of the tracking target candidate.

(14)

The medical observation system according to any one of (1) to (13), wherein the recognition reliability includes recognition reliability for a type of the tracking target candidate.

(15)

The medical observation system according to any one of (1) to (14), wherein the display unit displays information for identifying a plurality of the tracking target candidate in superposition with the operative field image.

(16)

The medical observation system according to any one of (1) to (15), wherein the display unit displays a position adjustment image for adjusting a position in a planar direction or a depth direction of the tracking target determined by the target determination unit so as to be superimposed on the operative field image.

(17)

The medical observation system according to (16), wherein the display unit displays the position adjustment image in accordance with the recognition reliability of the tracking target candidate recognized by the target candidate recognition unit.

(18)

The medical observation system according to any one of (1) to (17), further comprising:

an input unit that receives information regarding a voice of the user or an input operation of the user; and a control unit that switches an automatic tracking state of tracking the tracking target, a voice input state of receiving a voice of the user, and an automatic tracking stop state in which tracking of the tracking target is stopped according to the information regarding the voice or the input operation.

(19)

The medical observation system according to any one of (1) to (18), further comprising:

an arm portion that supports and moves the imaging unit; and an arm control unit that controls the arm portion such that the tracking target determined by the target determination unit is positioned in the operative field image.

(20)

The medical observation system according to (19), further comprising an input unit that receives information regarding an operation of the arm portion, wherein the arm control unit controls the arm portion on a basis of the information regarding the operation of the arm portion.

(21)

The medical observation system according to any one of (1) to (20), further comprising an image processing unit that generates the operative field image such that the tracking target determined by the target determination unit is positioned in the operative field image.

(22)

An information processing apparatus comprising:

a target candidate recognition unit that recognizes a tracking target candidate from an operative field image acquired by an imaging unit that acquires the operative field image including an abdominal cavity environment;

a reliability acquisition unit that acquires recognition reliability of the tracking target candidate recognized by the target candidate recognition unit;

a gaze information acquisition unit that acquires information regarding gaze of a user on the abdominal cavity environment of the operative field image displayed by a display unit that displays the operative field image acquired by the imaging unit; and a tracking target determination unit that determines a tracking target in the abdominal cavity environment from the tracking target candidate on a basis of the information regarding the tracking target candidate recognized by the target candidate recognition unit, the recognition reliability acquired by the reliability acquisition unit, and the information regarding the gaze acquired by the gaze information acquisition unit.

(23)

An information processing method comprising:

recognizing a tracking target candidate from an operative field image acquired by an imaging unit that acquires the operative field image including an abdominal cavity environment;

acquiring recognition reliability of the tracking target candidate recognized;

acquiring information regarding gaze of a user on the abdominal cavity environment of the operative field image displayed by a display unit that displays the operative field image acquired by the imaging unit; and determining a tracking target in the abdominal cavity environment from the tracking target candidate on a basis of the information regarding the tracking target candidate recognized, the recognition reliability acquired, and the information regarding the gaze acquired.

(24)

A medical observation method using the medical observation system according to any one of (1) to (21).

(25)

An information processing apparatus using the medical observation system according to any one of (1) to (21).

(26)

An information processing method using the medical observation system according to any one of (1) to (21).

REFERENCE SIGNS LIST

1000 ENDOSCOPIC SURGERY SYSTEM
1001 ENDOSCOPE
1003 LENS BARREL
1005 CAMERA HEAD
1007 LENS UNIT
1009 IMAGING UNIT
1011 DRIVE UNIT
1013 COMMUNICATION UNIT
1015 CAMERA HEAD CONTROL UNIT
1017 SURGICAL TOOL
1019 PNEUMOPERITONEUM TUBE
1021 ENERGY TREATMENT TOOL
1023 FORCEPS
1025a TROCAR
1025b TROCAR
1025c TROCAR
1025d TROCAR
1027 SUPPORT ARM DEVICE
1029 BASE PORTION
1031 ARM PORTION
1033a JOINT PORTION
1033b JOINT PORTION
1033c JOINT PORTION
1035a LINK
1035b LINK
1037 CART
1039 CCU
1041 DISPLAY DEVICE
1043 LIGHT SOURCE DEVICE
1045 ARM CONTROL DEVICE
1047 INPUT DEVICE
1049 TREATMENT TOOL CONTROL DEVICE
1051 PNEUMOPERITONEUM DEVICE
1053 RECORDER
1055 PRINTER
1057 FOOT SWITCH
1059 COMMUNICATION UNIT

1061 IMAGE PROCESSING UNIT
1063 CONTROL UNIT
1065 TRANSMISSION CABLE
1066 TRANSMISSION CABLE
1067 OPERATOR
1069 PATIENT BED
1071 PATIENT
2001 TARGET CANDIDATE RECOGNITION UNIT
2002 RELIABILITY ACQUISITION UNIT
2003 TARGET DETERMINATION UNIT
2010 LINE-OF-SIGHT INFORMATION PROCESSING UNIT
2020 VOICE RECOGNITION UNIT
2100 LINE-OF-SIGHT ACQUISITION UNIT
2101 COMMUNICATION UNIT
2102 LINE-OF-SIGHT DETECTION UNIT
2200 VOICE ACQUISITION UNIT
2201 COMMUNICATION UNIT
2202 VOICE DETECTION UNIT

The invention claimed is:

1. A medical observation system comprising:

an imaging unit that acquires an operative field image including an abdominal cavity environment;

a display unit that displays the operative field image acquired by the imaging unit;

a gaze information acquisition unit that acquires information regarding gaze of a user on the abdominal cavity environment of the operative field image displayed by the display unit;

a target candidate recognition unit that recognizes a tracking target candidate from the operative field image acquired by the imaging unit;

a reliability acquisition unit that acquires recognition reliability of the tracking target candidate recognized by the target candidate recognition unit; and a target determination unit that determines a tracking target in the abdominal cavity environment from the tracking target candidate on a basis of the information regarding the tracking target candidate recognized by the target candidate recognition unit, the recognition reliability acquired by the reliability acquisition unit, and the information regarding the gaze acquired by the gaze information acquisition unit.

2. The medical observation system according to claim 1, wherein the target determination unit determines the tracking target from the tracking target candidate according to a predetermined threshold of the recognition reliability preset.

3. The medical observation system according to claim 2, wherein the target determination unit uses the information regarding the gaze in a case where the recognition reliability acquired by the reliability acquisition unit is less than the predetermined threshold.

4. The medical observation system according to claim 1, wherein the information regarding the tracking target candidate includes information regarding a recognition region of the tracking target candidate, the information regarding the gaze includes information regarding a gaze region of the user, and the target determination unit determines the tracking target according to an overlapping area of the recognition region and the gaze region.

5. The medical observation system according to claim 4, wherein the target determination unit calculates an overlapping area between the recognition region and the gaze region for each of the tracking target candidate, and determines the tracking target candidate having the overlapping area being largest as the tracking target.

6. The medical observation system according to claim 1, further comprising an input unit that receives information regarding a voice of the user and an operation of the tracking target candidate.

7. The medical observation system according to claim 6, wherein the target determination unit determines the tracking target on a basis of at least one of the information regarding the voice of the user or the information regarding the operation of the tracking target candidate.

8. The medical observation system according to claim 7, wherein the information regarding the voice of the user is a correction request, and the target determination unit determines the tracking target candidate having the recognition reliability being higher as the tracking target in response to the correction request.

9. The medical observation system according to claim 1, wherein the target determination unit determines continuation and stop of processing of determining the tracking target according to whether or not the tracking target is at a predetermined expected position.

10. The medical observation system according to claim 1, wherein the target determination unit determines the tracking target on a basis of the information regarding the gaze in a case where the target determination unit cannot acquire the information regarding the tracking target candidate.

11. The medical observation system according to claim 1, wherein the target candidate recognition unit recognizes the tracking target candidate on a basis of the information regarding the gaze.

12. The medical observation system according to claim 1, wherein the recognition reliability is a probability indicating whether or not the tracking target candidate is within a predetermined target region.

13. The medical observation system according to claim 1, wherein the recognition reliability includes recognition reliability with respect to a position in a planar direction or a depth direction of the tracking target candidate.

14. The medical observation system according to claim 1, wherein the recognition reliability includes recognition reliability for a type of the tracking target candidate.

15. The medical observation system according to claim 1, wherein the display unit displays information for identifying a plurality of the tracking target candidate in superposition with the operative field image.

16. The medical observation system according to claim 1, wherein the display unit displays a position adjustment image for adjusting a position in a planar direction or a depth direction of the tracking target determined by the target determination unit so as to be superimposed on the operative field image.

17. The medical observation system according to claim 16, wherein the display unit displays the position adjustment image in accordance with the recognition reliability of the tracking target candidate recognized by the target candidate recognition unit.

18. The medical observation system according to claim 1, further comprising:

an input unit that receives information regarding a voice of the user or an input operation of the user; and a control unit that switches an automatic tracking state of tracking the tracking target, a voice input state of receiving a voice of the user, and an automatic tracking stop state in which tracking of the tracking target is stopped according to the information regarding the voice or the input operation.

19. The medical observation system according to claim 1, further comprising:

an arm portion that supports and moves the imaging unit; and an arm control unit that controls the arm portion such that the tracking target determined by the target determination unit is positioned in the operative field image.

20. The medical observation system according to claim 19, further comprising an input unit that receives information regarding an operation of the arm portion, wherein the arm control unit controls the arm portion on a basis of the information regarding the operation of the arm portion.

21. The medical observation system according to claim 1, further comprising an image processing unit that generates the operative field image such that the tracking target determined by the target determination unit is positioned in the operative field image.

22. An information processing apparatus comprising:

a target candidate recognition unit that recognizes a tracking target candidate from an operative field image acquired by an imaging unit that acquires the operative field image including an abdominal cavity environment;

a reliability acquisition unit that acquires recognition reliability of the tracking target candidate recognized by the target candidate recognition unit;

a gaze information acquisition unit that acquires information regarding gaze of a user on the abdominal cavity environment of the operative field image displayed by a display unit that displays the operative field image acquired by the imaging unit; and a tracking target determination unit that determines a tracking target in the abdominal cavity environment from the tracking target candidate on a basis of the information regarding the tracking target candidate recognized by the target candidate recognition unit, the recognition reliability acquired by the reliability acquisition unit, and the information regarding the gaze acquired by the gaze information acquisition unit.

23. An information processing method comprising:

recognizing a tracking target candidate from an operative field image acquired by an imaging unit that acquires the operative field image including an abdominal cavity environment;

acquiring recognition reliability of the tracking target candidate recognized;

acquiring information regarding gaze of a user on the abdominal cavity environment of the operative field image displayed by a display unit that displays the operative field image acquired by the imaging unit; and determining a tracking target in the abdominal cavity environment from the tracking target candidate on a basis of the information regarding the tracking target candidate recognized, the recognition reliability acquired, and the information regarding the gaze acquired.

\* \* \* \* \*